(12) United States Patent
Stetson

(10) Patent No.: US 8,764,189 B2
(45) Date of Patent: Jul. 1, 2014

(54) METHODS FOR MAPPING TISSUE WITH OPTICAL COHERENCE TOMOGRAPHY DATA

(75) Inventor: Paul F. Stetson, Oakland, CA (US)

(73) Assignee: Carl Zeiss Meditec, Inc., Dublin, CA (US)

(*) Notice: Subject to any disclaimer, the term of this patent is extended or adjusted under 35 U.S.C. 154(b) by 0 days.

(21) Appl. No.: 13/240,701

(22) Filed: Sep. 22, 2011

(65) Prior Publication Data

US 2012/0075584 A1 Mar. 29, 2012

Related U.S. Application Data

(62) Division of application No. 12/822,054, filed on Jun. 23, 2010, now Pat. No. 8,045,176, which is a division of application No. 11/717,263, filed on Mar. 13, 2007, now Pat. No. 7,768,652.

(60) Provisional application No. 60/782,840, filed on Mar. 16, 2006, provisional application No. 60/795,911, filed on Apr. 28, 2006, provisional application No. 60/815,107, filed on Jun. 20, 2006, provisional application No. 60/854,872, filed on Oct. 27, 2006, provisional application No. 60/857,451, filed on Nov. 7, 2006.

(51) Int. Cl.
*A61B 3/10* (2006.01)
*A61B 3/00* (2006.01)

(52) U.S. Cl.
CPC .... *A61B 3/10* (2013.01); *A61B 3/00* (2013.01)
USPC .......................................... 351/205; 351/246

(58) Field of Classification Search
USPC ........................................ 351/205, 206, 246
See application file for complete search history.

(56) References Cited

U.S. PATENT DOCUMENTS

| 4,838,679 A | 6/1989 | Bille |
| 5,293,871 A | 3/1994 | Reinstein et al. |
| 5,321,501 A | 6/1994 | Swanson et al. |

(Continued)

FOREIGN PATENT DOCUMENTS

| CA | 2390072 A1 | 12/2003 |
| EP | 0415683 A2 | 3/1991 |
| WO | 2004/043245 A1 | 5/2004 |
| WO | 2004/102112 A1 | 11/2004 |

OTHER PUBLICATIONS

Burgoyne, et al, Three-Dimensional Reconstruction of Normal and Early Glaucoma Monkey Optic Nerve Head Connective Tissues, Dec. 2004, Association for Research in Vision and Ophthalmology, Investigative Ophthalmology & Visual Science, Dec. 2004, vol. 45, No. 12 pp. 4388-4399.*

(Continued)

*Primary Examiner* — James Greece
(74) *Attorney, Agent, or Firm* — Morrison & Foerster LLP

(57) ABSTRACT

Various methods are disclosed for mapping optical coherence tomography (OCT) data to facilitate review and diagnosis. In one aspect, high resolution 2D line scans are obtained along with lower density 3D cube scans and displayed in a manner to provide context to the clinician. In another aspect, OCT data is analyzed to provide information about non-uniformities of the tissue. Binary image maps of maps useful for determining tautness of membranes are also disclosed.

25 Claims, 22 Drawing Sheets
(17 of 22 Drawing Sheet(s) Filed in Color)

(56) References Cited

U.S. PATENT DOCUMENTS

| | | | |
|---|---|---|---|
| 5,459,570 | A | 10/1995 | Swanson et al. |
| 5,465,147 | A | 11/1995 | Swanson |
| 5,562,095 | A | 10/1996 | Downey et al. |
| 5,861,955 | A | 1/1999 | Gordon |
| 5,921,926 | A | 7/1999 | Rolland et al. |
| 5,975,697 | A | 11/1999 | Podoleanu et al. |
| 6,165,142 | A | 12/2000 | Bar |
| 6,201,989 | B1 | 3/2001 | Whitehead et al. |
| 6,260,968 | B1 | 7/2001 | Stark et al. |
| 6,609,793 | B2 | 8/2003 | Norrby et al. |
| 6,769,769 | B2 | 8/2004 | Podoleanu et al. |
| 6,927,860 | B2 | 8/2005 | Podoleanu et al. |
| 7,145,661 | B2 | 12/2006 | Hitzenberger |
| 7,194,117 | B2 | 3/2007 | Kaufman et al. |
| 7,301,644 | B2 | 11/2007 | Knighton et al. |
| 7,364,296 | B2 | 4/2008 | Miller et al. |
| 7,365,856 | B2 | 4/2008 | Everett et al. |
| 7,433,046 | B2 | 10/2008 | Everett et al. |
| 7,466,423 | B2 | 12/2008 | Podoleanu et al. |
| 7,474,407 | B2 | 1/2009 | Gutin |
| 7,505,142 | B2 | 3/2009 | Knighton et al. |
| 7,616,799 | B2 | 11/2009 | Ramamurthy et al. |
| 7,659,990 | B2 | 2/2010 | Knighton et al. |
| 7,830,525 | B2 | 11/2010 | Buckland et al. |
| 7,884,945 | B2 | 2/2011 | Srinivasan et al. |
| 7,901,080 | B2 | 3/2011 | Hauger et al. |
| 7,924,429 | B2 | 4/2011 | Knighton et al. |
| 2003/0199769 | A1 | 10/2003 | Podoleanu et al. |
| 2004/0036838 | A1 | 2/2004 | Podoleanu et al. |
| 2004/0133112 | A1 | 7/2004 | Rajadhyaksha |
| 2004/0233457 | A1 | 11/2004 | Podoleanu et al. |
| 2004/0239938 | A1 | 12/2004 | Izatt |
| 2005/0048044 | A1* | 3/2005 | Schwartz et al. ............ 424/94.1 |
| 2005/0096515 | A1 | 5/2005 | Geng |
| 2005/0254009 | A1 | 11/2005 | Baker et al. |
| 2006/0066869 | A1 | 3/2006 | Ueno et al. |
| 2006/0072424 | A1 | 4/2006 | Everett et al. |
| 2006/0119858 | A1 | 6/2006 | Knighton et al. |
| 2006/0132790 | A1 | 6/2006 | Gutin |
| 2006/0164639 | A1 | 7/2006 | Horn et al. |
| 2006/0164653 | A1 | 7/2006 | Everett et al. |
| 2006/0187462 | A1 | 8/2006 | Srinivasan et al. |
| 2006/0228011 | A1 | 10/2006 | Everett et al. |
| 2007/0012886 | A1 | 1/2007 | Tearney et al. |
| 2007/0025642 | A1 | 2/2007 | Buckland et al. |
| 2007/0030483 | A1 | 2/2007 | Everett et al. |
| 2007/0103693 | A1 | 5/2007 | Everett et al. |
| 2007/0115481 | A1* | 5/2007 | Toth et al. ............ 356/511 |
| 2007/0216909 | A1 | 9/2007 | Everett et al. |

OTHER PUBLICATIONS

Williams et al, Characterization of Epiretinal Membrane Using Optical Coherence Tomography, Ophthalmology vol. 103, No. 12, Dec. 1996.*
Hitzenberger et al., "Three-dimensional imaging of the human retina by high-speed optical coherence tomography", Optics Express, vol. 11, No. 21, Oct. 20, 2003, pp. 2753-2761.
Leitgeb et al., "Performance of fourier domain vs. time domain optical coherence tomography", Optics Express, vol. 11, No. 8, Apr. 21, 2003, pp. 889-894.
De Boer et al., "Improved signal-to-noise ratio in spectral-domain compared with time domain optical coherence tomography", Optics Letters, vol. 28, No. 21, Nov. 1, 2003, pp. 2067-2069.
Wojtkowski et al., "Three-dimensional Retinal Imaging with High-Speed Ultrahigh Resolution Optical Coherence Tomography", Ophthalmology, vol. 112, No. 10, Oct. 2005, pp. 1734-1746.
Alam et al., "Clinical Application of Rapid Serial Fourier-Domain Optical Coherence Tomography for Macular Imaging", Ophthalmology, vol. 113, No. 8, Aug. 2006, pp. 1425-1431.
Costa et al., "Retinal assessment using optical coherence tomography", Progress in Retinal and Eye Research, 2006, vol. 25, No. 3, 29 pages in length.
Jiao et al., "Simultaneous acquisition of sectional and fundus ophthalmic images with spectral-domain optical coherence tomography", Optics Express, vol. 13, No. 2, Jan. 24, 2005, pp. 444-452.
Mujat et al., "Retinal nerve fiber layer thickness map determined from optical coherence tomography images", Optics Express, vol. 13, No. 23, Nov. 14, 2005, pp. 9480-9491.
Nassif et al., "In vivo human retinal imaging by ultrahigh-speed spectral domain optical coherence tomography", Optics Letters, vol. 29, No. 5, Mar. 1, 2004, pp. 480-482.
Paunescu et al., "Reproducibility of Nerve Fiber Thickness, Macular Thickness, and Optic Nerve Head Measurements Using StratusOCT", Investigative Ophthalmology & Visual Science, vol. 45, No. 6, Jun. 2004, pp. 1716-1724.
Sadda et al., "Automated Detection of Clinically Significant Macular Edema by Grid Scanning Optical Coherence Tomography", Ophthalmology, vol. 113, No. 7, Jul. 2006, pp. 1187-1196.
Schmidt-Erfurth et al., "Three-Dimensional Ultrahigh-Resolution Optical Coherence Tomography of Macular Diseases", Investigative Ophthalmology & Visual Science, vol. 46, No. 9, Sep. 2005, pp. 3393-3402.
Zhou et al., "Mapping retinal thickness and macular edema by high-speed three dimensional optical coherence tomography", Ophthalmic Technologies XIV—Proceedings of SPIE, vol. 5314 (SPIE, Bellingham, WA 2004), pp. 119-125.
Nov. 2006 Brochure by Heidelberg Engineering, "Bringing two views together SPECTRALS™ HRA+ OCT", 6 pages in length.
Nov. 2005 Brochure by OTI Ophthalmic Technologies Inc., "OTI OCT/SLO Combination Imaging System", 6 pages in length.
Oct. 2006 Brochure by Optovue Inc., "RTVue-100 -In-Vivo Histology (Fourier Domain OCT)", 6 pages in length.
Apr. 2004 User Manual by Carl Zeiss Meditec Inc., entitled "STRATUS OCT™—Model 3000", 190 pages in length.
Sep. 2005 User Manual by OTI Ophthalmic Technologies Inc., entitled "OCT/SLO Combination Imaging System", 79 pages in length.
Notice of Allowance received for U.S. Appl. No. 11/717,263, mailed on Mar. 23, 2010, 6 pages.
Fercher et al., "Optical coherence tomography—principles and applications", Reports on Progress in Physics, vol. 66, 2003, pp. 239-303.
Koozekanani et al., "Tracking the OPtic Nervehead in OCT Video Using Dual Eigenspaces and an Adaptive Vascular Distrubution Model", IEEE Transactions on Medical Imaging, vol. 22, No. 12, Dec. 2003, pp. 1519-1536.
Non Final Office Action received for U.S. Appl. No. 12/822,054, mailed on Apr. 5, 2011, 14 pages.
Notice of Allowance received for U.S. Appl. No. 12/822,054, mailed on Jul. 26, 2011, 21 pages.
Nassif et al., "In Vivo High-Resolution Video-Rate Spectral-Domain Optical Coherence Tomography of the Human Retina and Optic Nerve", Optics Express, vol. 12, No. 3, Feb. 9, 2004, pp. 367-376.
Choma et al., "Sensitivity Advantage of Swept Source and Fourier Domain Optical Coherence Tomography", Optics Express, vol. 11, No. 18, Sep. 8, 2003, pp. 2183-2189.
Huang et al., "Optical Coherence Tomography", Science, vol. 254, Nov. 22, 1991, pp. 1178-1181.
Office Action received for European Patent Application No. 05815426.1, mailed on Jan. 13, 2011, 3 pages.
International Search Report and Written Opinion received for PCT Patent Application No. PCT/EP2005/012801, mailed on Mar. 23, 2006, 9 pages.
Non Final Office Action received for U.S. Appl. No. 12/644,526, mailed on Sep. 1, 2010, 18 pages.
Notice of Allowance received for U.S. Appl. No. 12/644,526, mailed on Feb. 7, 2011, 9 pages.
Non Final Office Action received for U.S. Appl. No. 12/709,234, mailed on Feb. 16, 2011, 6 pages.
Notice of Allowance received for U.S. Appl. No. 12/644,526, mailed on Feb. 24, 2011, 7 pages.
Notice of Allowance received for U.S. Appl. No. 12/709,234, mailed on Jul. 28, 2011, 10 pages.

(56) References Cited

OTHER PUBLICATIONS

Notice of Allowance received for U.S. Appl. No. 13/283,445, mailed on Feb. 23, 2012, 10 pages.
Non-Final Office Action received for U.S. Appl. No. 13/043,401, mailed on Mar. 26, 2012, 22 pages.
Notice of Allowance received for U.S. Appl. No. 13/043,401, mailed on Jul. 27, 2012, 7 pages.
Notice of Allowance received for U.S. Appl. No. 13/488,280, mailed on Dec. 10, 2012, 10 pages.
Adaikkappan, et al., "Evaluation of Carotid Atherosclerosis by B'mode Ultrasonographic Study in Hypertensive Patients Compared with Normotensive Patients", Ind. J. Radiol. Imag., vol. 12, No. 3, 2002, pp. 365-368.
Bajraszewski, Tomasz, "Optical CoherenceTomography 3D Measurements in Vivo", ICPS, 2003, 16 pages.
Bajraszewski et al., "Three-Dimensional in Vivo Imaging by Spectral OCT", Proc. of SPIE, vol. 5316, 2004, pp. 226-232.
Bartsch et al., "Optical Coherence Tomography: Interpretation Artifacts and New Algorithm", Proc. SPIE Medical Imaging 2004: Image Processing, vol. 5370, 2004, pp. 2140-2151.
Boppart et al., "Noninvasive Assessment of the Developing Xenopus Cardiovascular System Using Optical Coherence Tomography", Proceedings of the National Academy of Sciences of the United States of America, vol. 94, Apr. 1997, pp. 4256-4261.
Boppart, Stephen Allen, "Surgical Diagnostics, Guidance, and Intervention using Optical Coherence Tomography", Massachusetts Institute of Technology, May 1998, 237 pages.
Bower et al., "Rapid Volumetric Imaging of the Human Retina in vivo Using a Low-Cost, Spectral-Domain Optical Coherence Tomography System", ARVO Annual Meeting, Program#/Poster#: 1050, printed from website, http://www.abstractsonline.comiviewerNiew/AbstractPrintFriendly on Jul. 26, 2005, May 2, 2005, 2 pages.
De Boer et al., "Ultra-High Speed and Ultra-High Resolution Structural, Flow Velocity, and Polarization Sensitive Sd/Fd-Oct and the Human Retina", ARVO Annual Meeting, Program#/Poster#: 1116, printed from website, http://www.abstractsonline.comiviewerNiewAbstractPrintFriendly on Jul. 26, 2005, May 2, 2005, 2 pages.
Dubois et al., "High-Resolution Three-Dimensional Imaging inside Biological Media Using White-Light Interference Microscopy", Proceedings of SPIE, vol. 5140, 2003, pp. 43-50.
Ferguson et al., "Enhanced Retinal Imaging With Tracking Optical Coherence Tomography (TOCT)", ARVO Annual Meeting, Program#/Poster#: 1118, printed from website, http://www.abstractsonline.comlviewer/ViewAbstractPrintFriendly on Jul. 26, 2005, May 2, 2005, 1 page.
Fujimoto, JG., "New Technology for Optical Coherence Tomography", table of contents title Advances in High Resolution and Spectral OCr, Ocular Imaging 2005, Palm Beach, Florida, Dec. 3-4, 2004, 8 pages.
Gregori et al., "3-D OCT Maps in Retinal Pathologies", ARVO Annual Meeting, Program#/ Poster#: 1055, printed from website, http://www.abstractsonline.com/viewer/ViewAbstractPrintFriendly on Jul. 26, 2005, May 2, 2005, 1 page.
Guirao et al., "Corneal Wave Aberration from Videokeratography: Accuracy and Limitations of the Procedure", J. Opt. Soc. Am. A. Vol 17, No. 6, Jun. 2000, pp. 955-965.
Everett et al., "Method of Bioimage Data Processing for Revealing more Meaningful Anatomic Features of Diseased Tissues" Unpublished U.S. Appl. No. 13/787,557, filed Mar. 6, 2013.
Ishikawa et al., "Macular Segmentation with Optical Coherence Tomography", Investigative Ophthalmology & Visual Science, vol. 46, No. 6, Jun. 2005, pp. 2012-2017.
Izatt et al., "Ophthalmic Diagnostics Using Optical Coherence Tomography,", Ophthalmic Technologies IIL SPIE, Los Angeles, CA, 1877, Jan. 16-18, 1993, pp. 136-144.
Jiao et al., "Macula Mapping and Simultaneous Acquisition of Sectional and Fundus Ophthalmic Images With Three-Dimensional Spectral-Domain Optical Coherence Tomography", ARVO Annual Meeting, Program#/Poster#: 1114, printed from website, http://www.abstractsonline.comlviewer/ ViewAbstractPrintFriendly on Jul. 26, 2005, May 2, 2005, 1 page.
Jiao et al., "Simultaneous Acquisition of Sectional and Fundus Images with Spectral-Domain Optical Coherence Tomography", Photonics West, Ophthalmic Technologies XV, Program #5688-81, Powerpoint presentation, Jan. 22, 2005, 21 pages.
Knighton et al., U.S. Appl. No. 60/632,387, filed Dec. 2, 2004, entitled "Enhanced Optical Coherence Tomography for Anatomical Mapping", 26 pages.
Ko et al., "Three Dimensional Retinal Imaging of Small Animals With High-speed, Ultrahigh Resolution Optical Coherence Tomography", ARVO Annual Meeting, Program#/Poster#: 1051, printed from website, http://www.abstractsonline.comiviewerNiewAbstractPrintFriendly on Jul. 26, 2005, May 2, 2005, 1 page.
Puliafito, CA, "Summary and Significance", American Academy of Ophthalmology Subspecialty Day on retina, Section X Ocular Imaging, New Orleans, Oct. 23, 2004, 16 pages.
Sacu, S., "Imaging and Pigment Epithelial Disease Using Three dimensional (3D) Ultrahigh Resolution (UHR) Optical Coherence Tomography (OCT)", ARVO Annual Meeting, Program#/Poster#: 2563/B116, printed from website, http://www.abstractsonline.comlviewer/ViewAbstractPrintFriendly on Jul. 26, 2005, May 3, 2005, 1 page.
Schmidt-Erfurth et al., "Three-Dimensional Ultrahigh Resolution Optical Coherence Tomography (3D UHR OCT): A Video Presentation", ARVO Annual Meeting, Program#/Poster#: 1115,, printed from website, http://www.abstractsonline.comiviewerNiewAbstractPrintFriendly on Jul. 26, 2005, May 2, 2005, 1 page.
Scholda et al., "Visualization of the Vitreoretinal Interface Using Three-Dimensional Ultrahigh Resolution Optical Coherence Tomography", ARVO Annual Meeting, Program#/Poster#: 1054,, printed from website, http://www.abstractsonline.comiviewerNiewAbstractPrintFriendly on Jul. 26, 2005, May 2, 2005, 1 page.
Sharp, P. F., "The Scanning Laser Ophthalmoscope—a Review of its Role in Bioscience and Medicine", Physics in Medicine and Biology, vol. 49, 2004, pp. 1085-1096.
Srinivasan et al., "Intraretinal Thickness Mapping using Three Dimensional, High-Speed Ultrahigh Resolution OCT", ARVO Annual Meeting, Program#/ Poster#: 1113, printed from website, http://www.abstractsonline.comiviewerNiewAbstractPrintFriendly on Jul. 26, 2005, May 2, 2005, 1 page.
Swanson et al., "In Vivo Retinal Imaging by Optical Coherencetomography", Optics Letters vol. 18 No. 21, Nov. 1, 1993, pp. 1864-1866.
Webb, Robert H., "Confocal Optical Microscopy", Rep. Frog. Phys., vol. 59, 1996, pp. 427-471.
Werner et al., "Three-Dimensional Retinal Imaging With High Speed and High Resolution OCT", ARVO Annual Meeting, Program#/ Poster#: 1052, printed from website, http://www.abstractsonline.comlviewer/ViewAbstractPrintFriendly on Jul. 26, 2005, May 2, 2005, 1 page.
Wojkowski, M., "Three-Dimensional Retinal Imaging with High-Speed Ultrahigh-Resolution Optical Coherence Tomography", American Journal of Ophthalmology, Ophthalmic Publ., Chicago, Illinois, Sep. 2004, pp. 1734-1746.
Wojtkowski et al., "Real-Time and Static in Vivo Ophthalmic Imaging by Spectral Optical Coherence Tomography", Proceedings of SPIE, vol. 5314, 2004, pp. 126-131.
Wojtkowski et al., "Ophthalmic Imaging by Spectral Optical Coherence Tomography", American Journal of Ophthalmology, Ophthalmic Publ., Chicago, IL vol. 138 No. 3, Sep. 2004, pp. 412-419.
Wojtkowski, Maciej, "Good Quality medical Imaging by Ultra-Fast Spectral OCT Device", MIT Presentation, Oct. 22, 2003, 36 pages.
Extended European Search Report (includes European Search Report and European Search Opinion) received for European Patent Application No. 13151051.3, mailed on Jul. 1, 2013, 7 pages.

* cited by examiner

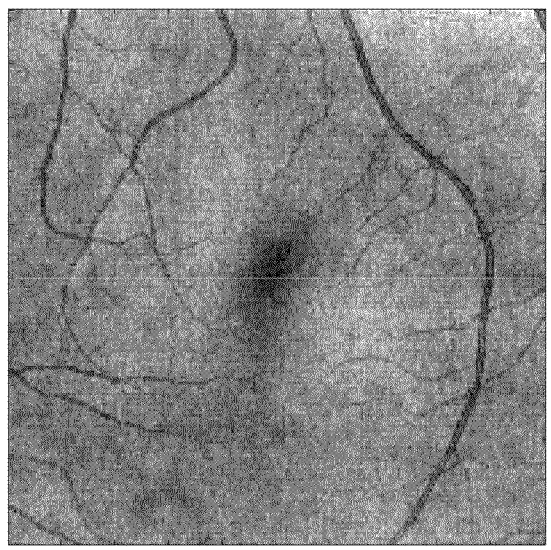
Fig. 1

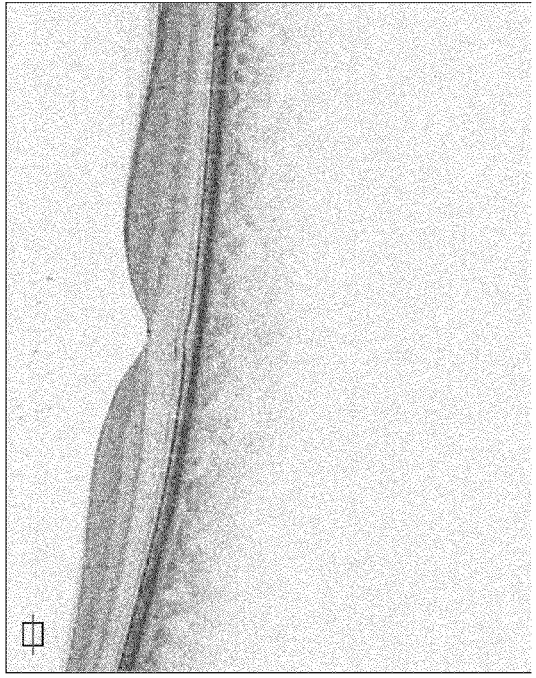
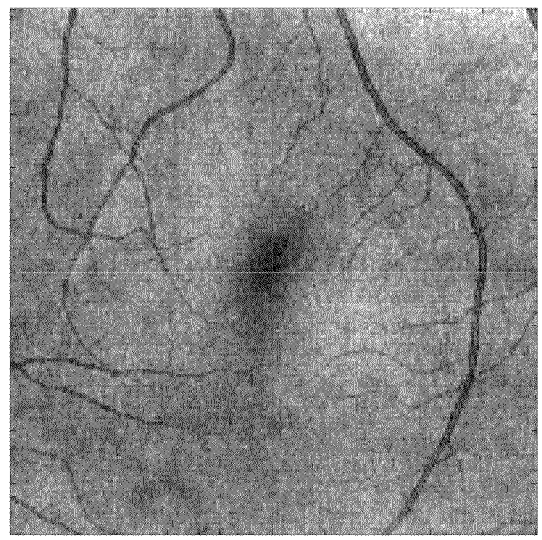
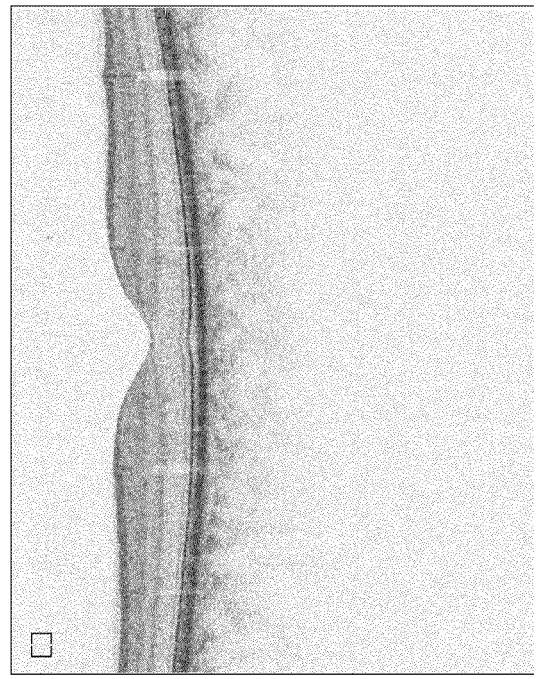
Fig. 2

Fig. 3 Tissue thickness maps derived form a 3D block of OCT data

Fig. 4 Two high-definition scans presented with surfaces extracted from the 3D block of OCT data

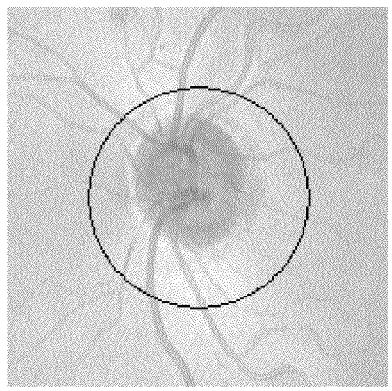 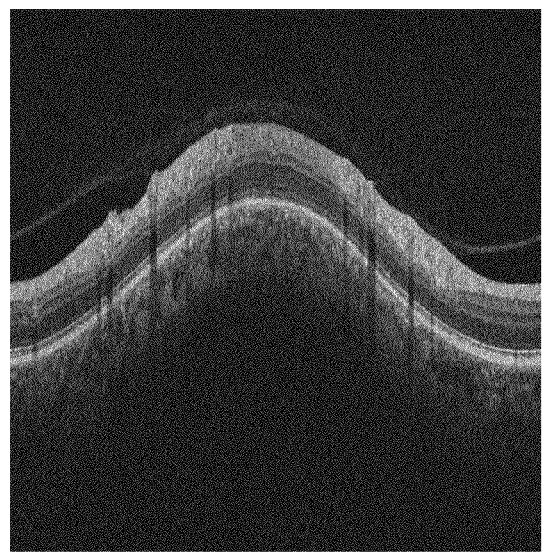
Fig. 5

Fig. 6a ophthalmoscope fundus image
Fig 6b overlay
Fig. 6c Live fundus image with saved image overlaid.
Fig. 6d Live fundus image with overlaid saved image aligned.

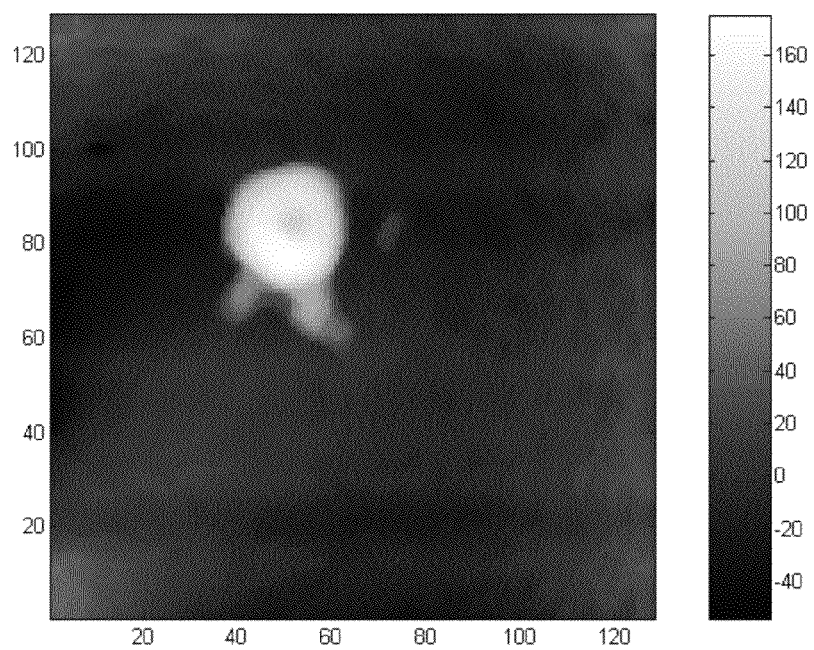
Fig. 9 An en-face map of RPE elevation in microns relative to a surface fitted to the RPE.

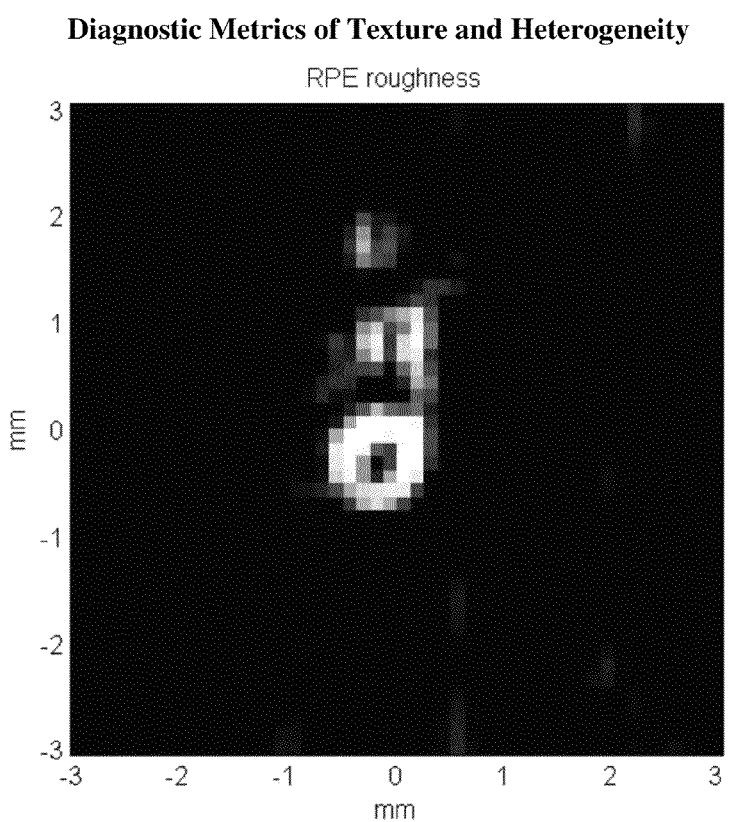
Fig. 10 En-face map showing root-mean-squared deviation of the RPE depth about the local mean depth.

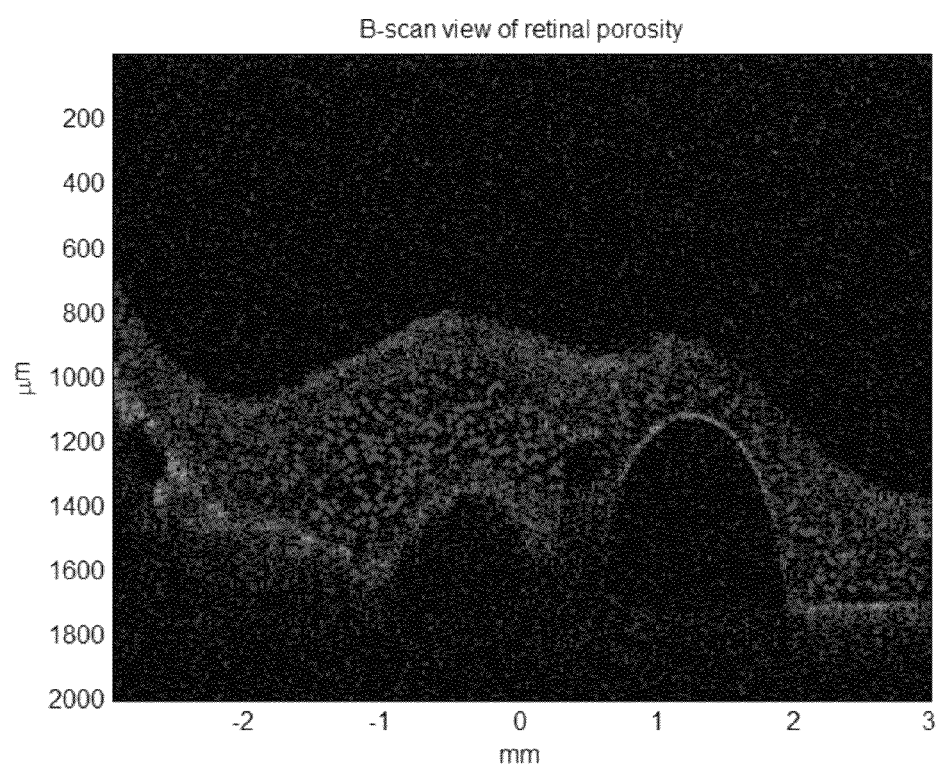
Fig. 11 B-scan showing the detection of small voids larger than the normal dark spots that are due to speckle

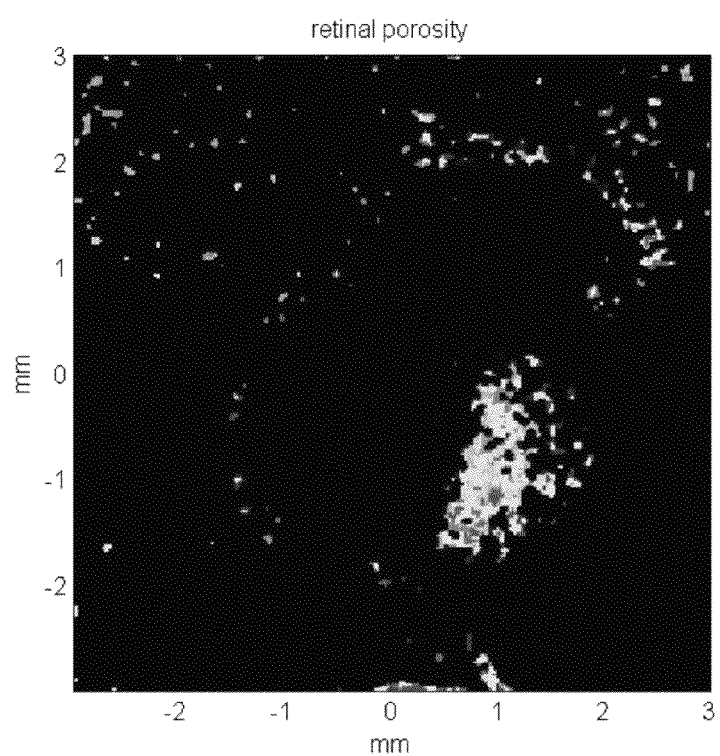
Fig. 12 En-face map showing the density of voids in the retina.
Yellow indicates an elevated density; red indicates the highest densities.

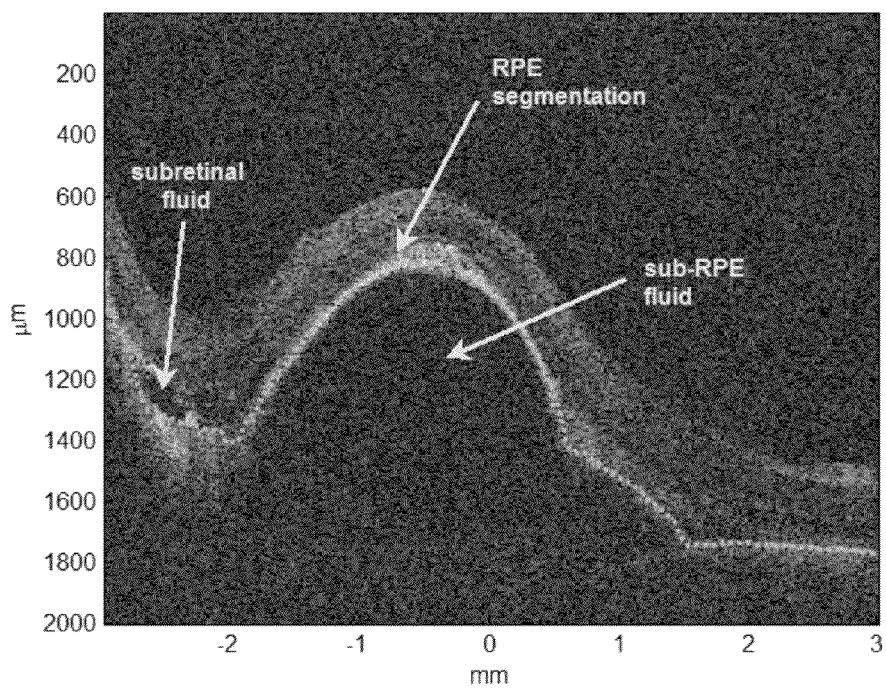
Fig. 13 B-scan showing the presence of fluid both below and above the RPE, but below the neurosensory retina.

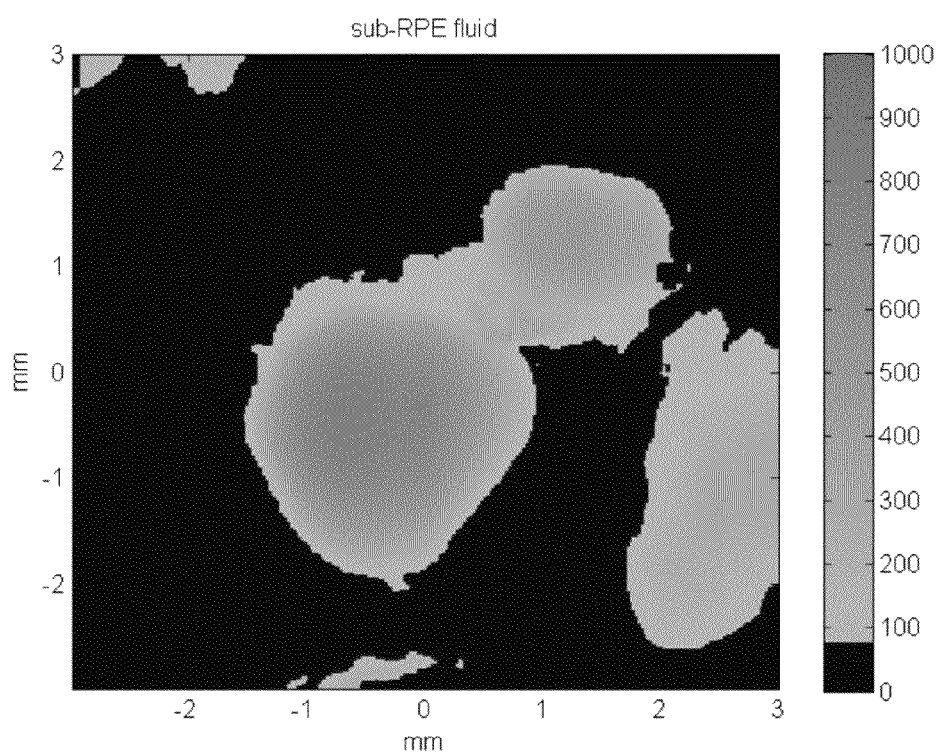
Fig. 14 En-face map showing the depth of fluid in microns between the RPE and a parabolic surface fitted to the RPE.

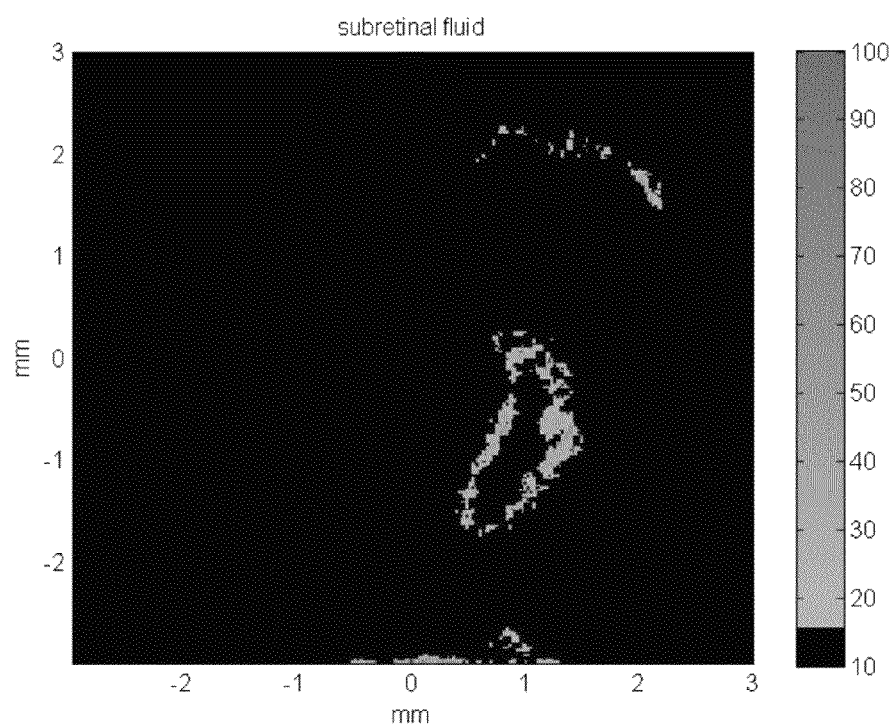
Fig. 15 En-face map showing the depth of fluid in microns in the vicinity just above the RPE.

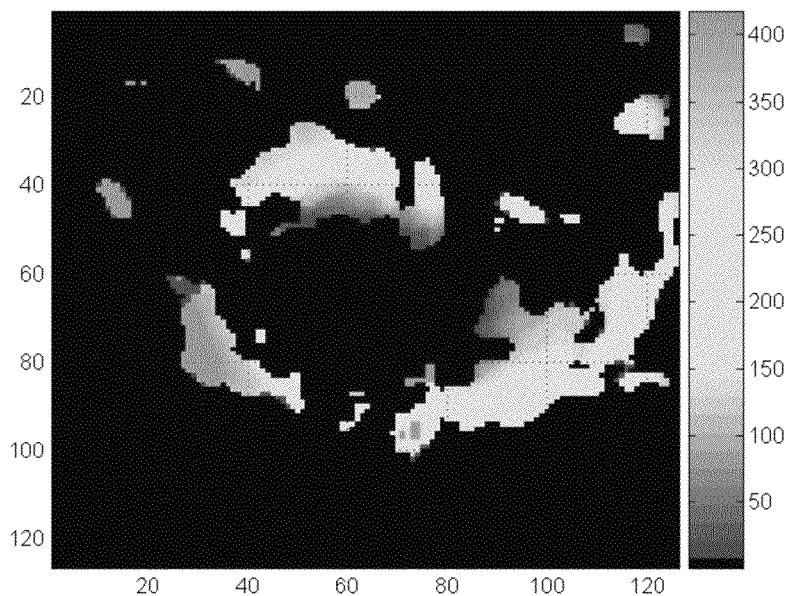
Fig. 16 An en-face view indicating points of membrane attachment.

3D Analysis of Membrane Geometry to identify Traction Forces
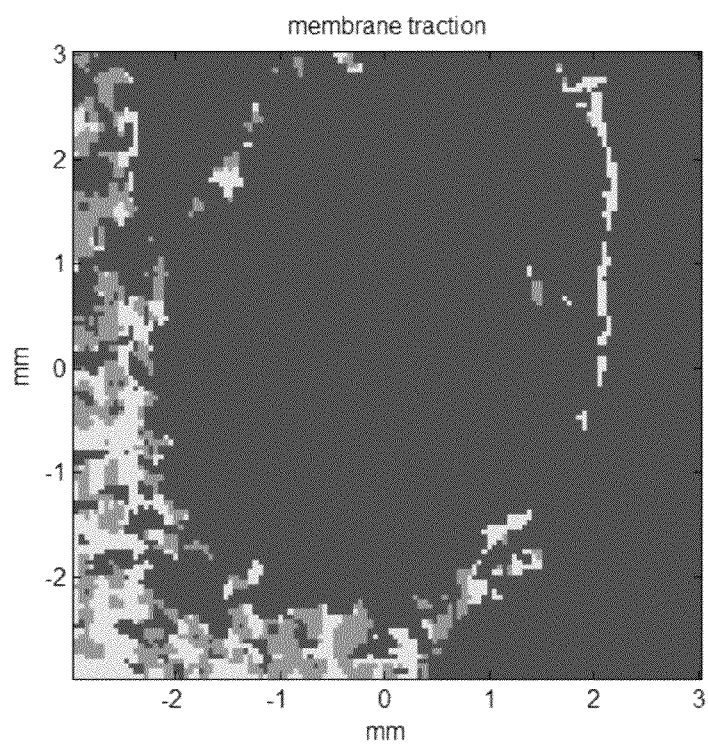
Fig. 17 En-face map showing points where membranes approach the vitreo-retinal interface (VRI) and the curvature of the VRI at that point.

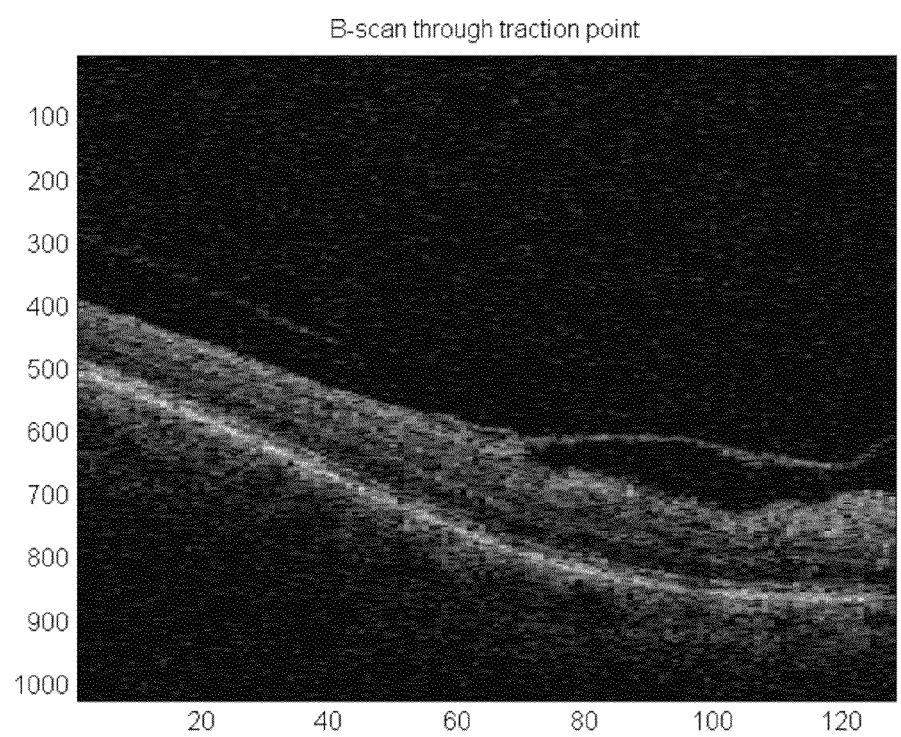
Fig. 18 Horizontal B-scan through a point of high membrane traction as indicated in red on the traction map above.

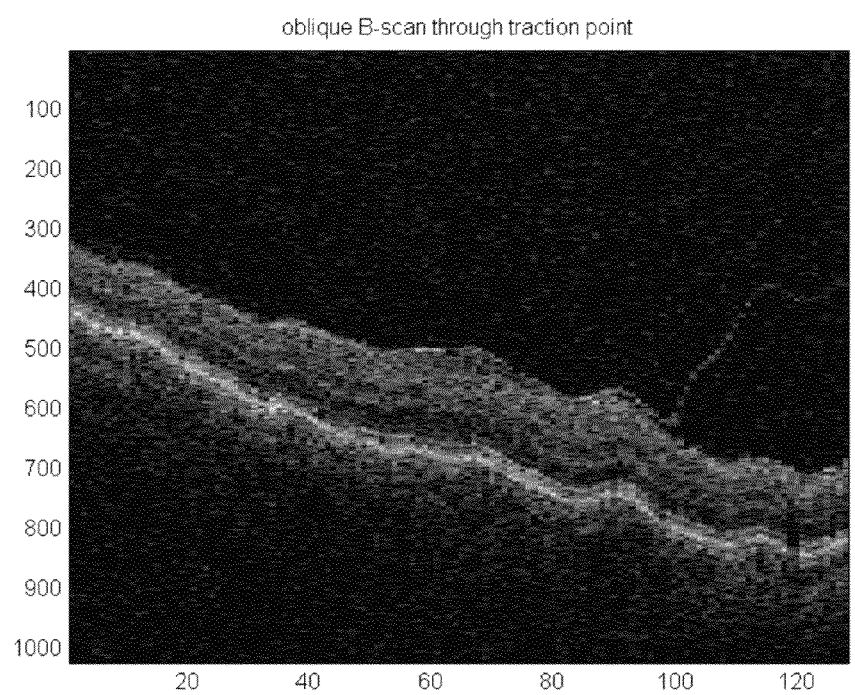
Fig. 19 Diagonal B-scan composed of lines extracted from a set of parallel horizontal B-scans. The direction of this B-scan is perpendicular to the ridge in the VRI.

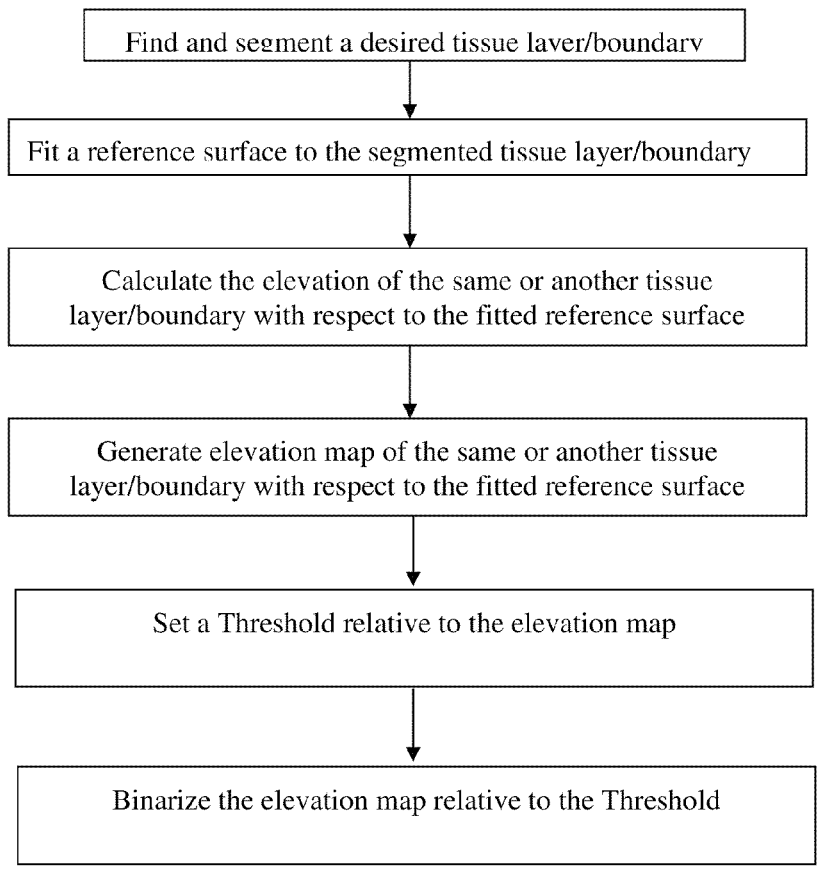
Fig. 20 Flowgraph for creating a binary

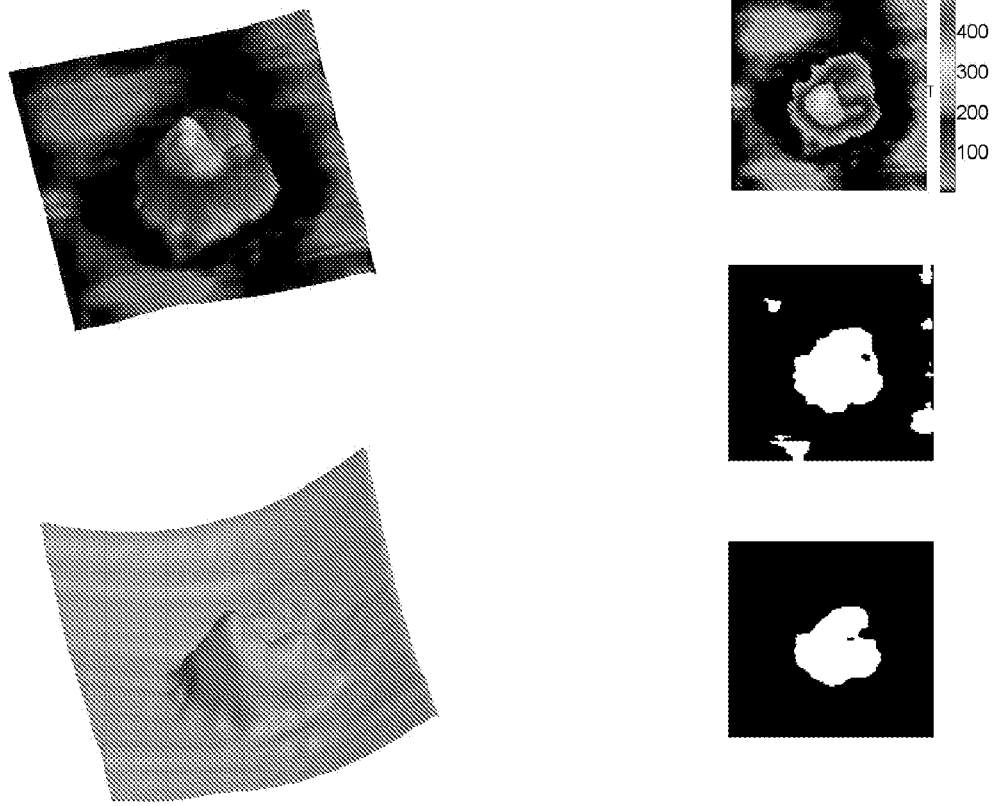
Fig. 21 RPE Analysis – case 1

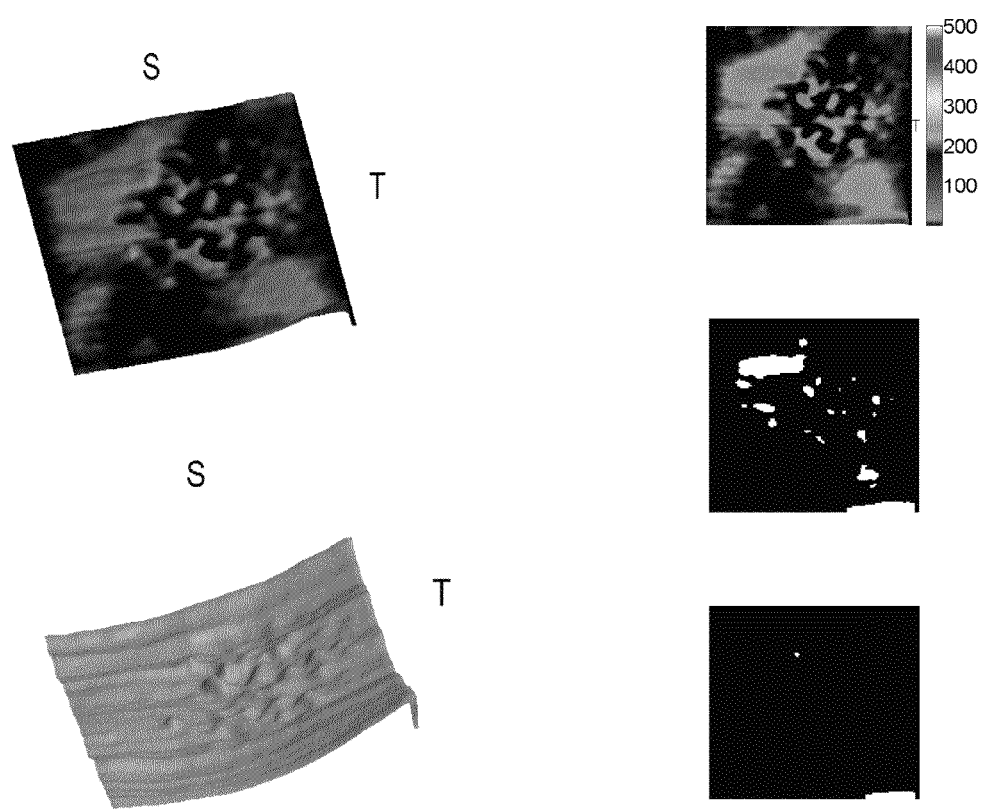
Fig. 22 RPE Analysis – case 2

METHODS FOR MAPPING TISSUE WITH OPTICAL COHERENCE TOMOGRAPHY DATA

PRIORITY INFORMATION

This divisional application claims priority to U.S. patent application Ser. No. 12/822,054, filed Jun. 23, 2010, which in turn claims priority to divisional application U.S. patent application Ser. No. 11/717,263, filed Mar. 13, 2007, which application in turn claims priority to: U.S. Provisional Application No. 60/782,840, filed Mar. 16, 2006; U.S. Provisional Application No. 60/795,911, filed Apr. 28, 2006; U.S. Provisional Application No. 60/815,107, filed Jun. 20, 2006; U.S. Provisional Application No. 60/854,872, filed Oct. 27, 2006, and U.S. Provisional Application No. 60/857,451, filed Nov. 7, 2006, all of which are incorporated by reference.

TECHNICAL FIELD

The present invention relates generally to methods for optical imaging of biological samples and for processing such images. In particular, the invention is in the field of three-dimensional imaging using Optical Coherence Tomography (OCT). Maps of elevation may be embodied as three-dimensional surface renderings of elevation, topographical maps, or as color or grayscale maps.

BACKGROUND

Optical Coherence Tomography (OCT) is a technique for performing high resolution cross-sectional imaging that can provide images of tissue structure on the micron scale in situ and in real time [Huang, D., E. A. Swanson, et al. *Science* 254 (5035): 1178-81]. OCT is a method of interferometry that determines the scattering profile of a sample along the OCT beam. Each scattering profile is called an axial scan, or A-scan. Cross-sectional images, and by extension 3D volumes, are built up from many A-scans, with the OCT beam moved to a set of transverse locations on the sample. Motion of the sample with respect to the OCT scanner will cause the actual locations measured on the sample to be arranged differently than the scan pattern in scanner coordinates, unless the motion is detected and the OCT beam placement corrected to track the motion.

In recent years, frequency domain OCT techniques have been applied to living samples [Nassif, N. A., B. Cense, et al. *Optics Express* 12(3): 367-376]. The frequency domain techniques have significant advantages in speed and signal-to-noise ratio as compared to time domain OCT [Leitgeb, R. A., et al. *Optics Express* 11(8): 889-894; de Boer, J. F. et al. *Optics Letters* 28: 2067-2069; Choma, M. A. and M. V. Sarunic *Optics Express* 11: 2183-2189]. The greater speed of modern OCT systems allows the acquisition of larger data sets, including 3D volume images of human tissue.

In the case of ophthalmology, a typical patient can comfortably hold his eye open for a few seconds. OCT systems can advantageously use these few seconds to collect extensive images [Hitzenberger, C. K. et al. "Three-dimensional imaging of the human retina by high-speed optical coherence tomography." *Optics Express* 11(21): 2753-2761, and "Spectral Radar: Optical Coherence Tomography in the Fourier Domain", Lindner, M. W., Andretzky, P., Kiesewetter, F., and Hausler, G. in B. E. Bouma and G. J. Tearney, Handbook of optical coherence tomography (Marcel Dekker, New York, 2002)].

Various approaches have been developed for analyzing and the displaying information obtained from OCT methods. For example, in U.S. patent application Ser. No. 11/223,549, filed Sep. 9, 2005 (and incorporated herein by reference), a method is disclosed for generating elevation maps or images of a tissue layer/boundary with respect to the location of a fitted reference surface, comprising the steps of finding and segmenting a desired tissue layer/boundary; fitting a smooth reference surface to the segmented tissue layer/boundary; calculating elevations of the same or other tissue layer/boundary relative to the fitted reference surface; and generating maps of elevation relative to the fitted surface.

The subject application relates to additional display methods which will facilitate the diagnosis and treatment of pathologies in the eye of a patient.

SUMMARY OF THE INVENTION

In one aspect of the subject invention, the OCT device is arranged to obtain both high resolution two dimensional scans (slices) as well as lower resolution three dimensional data cubes. In a preferred embodiment, information from both types of scans is displayed so that the lower resolution three dimensional scan can provide context or location cues for the higher resolution scans.

In another aspect of the subject invention, image data from a first measurement can be displayed in conjunction with image data from a second, later measurement to help align the patient with the device. This aspect can be particularly useful when the two measurements are taken during different visits to the clinician.

In another aspect of the subject invention, the system is configured to control the orientation of displayed images. The orientation can be selected using various criteria such as providing a consistent view or to better display features within the image.

In another aspect of the subject invention, maps are generated which show non-uniformities of features within the sample such as the eye. Such an approach can be useful to show textural features which can be correlated to various disease states such as the presence of drusen or exudates.

In another aspect of the subject invention, maps can be generated which can illustrate the connections between membranes and tissue layers such as the retina. Such maps can be useful to determine characteristics such as the disruption or curvature of tissue layers or tautness of the membranes.

In another aspect of the subject invention, image and/or map information is compared to a threshold with the results then being displayed as a binary map.

Further objects and advantages of the subject invention will become apparent from the following detailed discussion taken in conjunction with the drawings in which:

BRIEF DESCRIPTION OF THE DRAWINGS

The patent or application file contains at least one photograph executed in color. Copies of this patent or patent application publication with color drawings will be provided by the Office upon request and payment of the necessary fee.

FIG. 1 is a display screen of an OCT system showing three windows and illustrating two high resolution scans and one lower resolution scan.

FIG. 2 is a display screen similar to FIG. 1 wherein the two high resolution scans are replaced by reverse video images.

FIG. 5 is a display showing an en face image on the left hand side coupled with a high resolution compound circle scan on the right hand side.

FIGS. 6a through 6d shows how an ophthalmoscope fundus image can be overlaid by an image derived from an OCT data scan acquired during a previous visit. The image overlay can be used to facilitate patient alignment.

FIG. 9 is an en face color map of RPE elevation in microns relative to a surface fitted to the RPE.

FIG. 10 is an en face map showing root-mean-squared deviation of the RPE depth about the local mean depth.

FIG. 11 is a B-scan showing the detection of small voids larger than the normal dark spots that are due to speckle.

FIG. 12 is an en face map showing the density of voids in the retina.

FIG. 13 is a B-scan showing the presence of fluid both below and above the RPE.

FIG. 14 is an en face map showing the depth of fluid in microns between the RPE and a parabolic surface fitted to the RPE.

FIG. 15 is an en face map showing the depth of fluid in microns in the vicinity just above the RPE.

FIG. 16 is an en face view indicating points of membrane attachment.

FIG. 17 is an en face map showing points where membranes approach the vitreo-retinal interface (VRI) and the curvature of the VRI at that point.

FIG. 18 is a horizontal B-scan through a point of high membrane traction.

FIG. 19 is a diagonal B-scan composed of lines extracted from a set of parallel horizontal B-scans.

FIG. 20 is a flow chart illustrating a sequence of steps to generate a binary map.

FIG. 21 are images including a color coded elevational map of the RPE as well as two binary images.

FIG. 22 are images including a color coded elevational map of the RPE as well as two binary images.

DETAILED DESCRIPTION OF THE PREFERRED EMBODIMENTS

Figure 3:
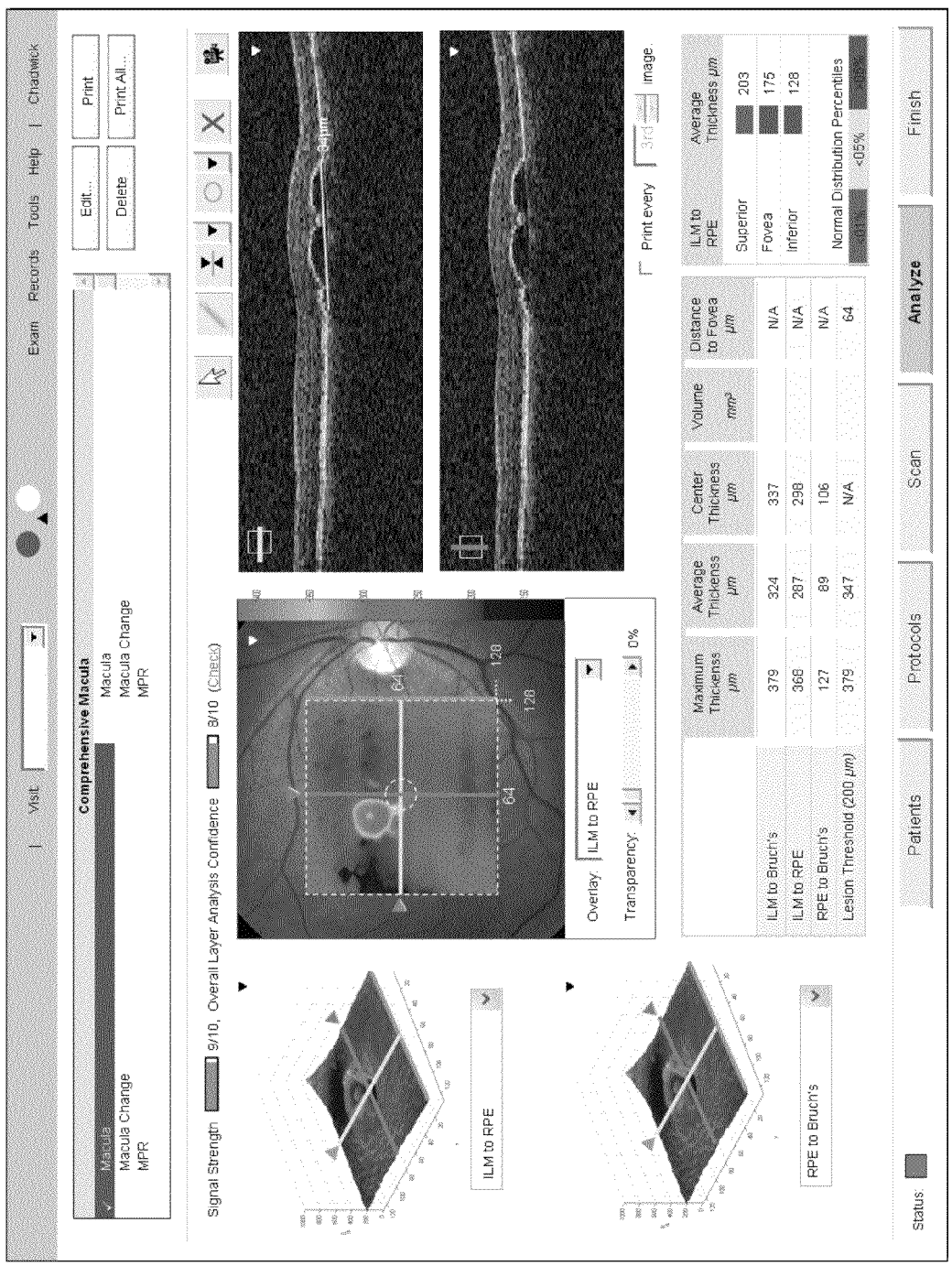
FIG. 3 is a display screen of an OCT system illustrating both high resolution scans, a lower resolution scan and a issue thickness overlay.

The approaches discussed herein are preferably implemented on a device for measuring samples using optical coherence tomography (OCT). One such device has been marketed for some time by the assignee herein under the trademark Stratus OCT. The assignee just recently introduced a new system under the trademark Cirrus HD-OCT. This device is a composite system which includes not only an OCT scanner but also an ophthalmoscope which is aligned with the OCT system along a common optical axis. A description of a system having both an OCT module and an ophthalmoscope is set forth in U.S. Patent Publication No. 2006/0228011, incorporated herein by reference.

The Cirrus device is a frequency domain OCT system with a broadband light source and a spectrometer. A preferred spectrometer system is described in U.S. Patent Publication No. 2007/0030483, which is incorporated herein by reference.

It is believed that the concepts discussed and claimed herein are independent of the specific hardware used to take the measurements and can be understood by one skilled in the art by reference to the various patents and publications cited above and listed below which are all incorporated herein by reference and include:

U.S. Patent Publication No. 2005/0254009
U.S. Patent Publication No. 2006/0164653
U.S. Patent Publication No. 2006/0164639

Although not required for an understanding of the inventions claimed herein, additional details of the assignee's Cirrus system are set forth in three provisional applications; U.S. Provisional Application No. 60/815,107, filed June 20, 2, U.S. Provisional Application No. 60/854,872 filed Oct. 27, 2006, and U.S. Provisional Application No. 60/857,451, filed Nov. 7, 2006, which are incorporated herein by reference.

Collection of Compound OCT Scans

The first embodiment of the subject invention relates to a method of acquiring OCT data sets to provide both high definition scan(s) and a lower resolution data cube within a short period of time so that the data cube provides context for the high definition scan(s).

Clinicians want to know where retinal OCT tomograms lie in relation to landmarks on the retina. In cases of retinal pathology, clinicians want to see a cross-section of the pathology in the context of a map of the retina. One example of this is a cross-section of retinal edema presented in the context of a retinal thickness map. In a preferred embodiment, two sequential scans of differing types (resolutions) are performed and simultaneously displayed, preferably on the same display. It is particularly advantageous when these two display types can be acquired using a single interaction with the user interface, say a single click or a single voice command.

In StratusOCT (Paunescu, L. A., J. S. Schuman, et al. "Reproducibility of nerve fiber thickness, macular thickness, and optic nerve head measurements using StratusOCT." *Invest Ophthalmol Vis Sci* 45(6): 1716-24) a nearly-simultaneous fundus image is captured with the OCT, showing the location of the OCT beam on the retina. Motion of the eye between the fundus image and OCT scan can affect the quality of correspondence. Simultaneity here simply means that data collection happens quickly enough that the side-by-side display of the two types of data are sufficiently synchronized that they present two views of the same object and structure.

Publications by Podoleanu (U.S. Patent Publication No. 2003/0199769), for example, suggest taking a Scanning Laser Ophthalmoscope (SLO) image point-by-point simultaneously with the OCT scan. This approach uses an additional imaging system consisting of a beam splitter and the SLO detector, and depends on hardware alignment between the OCT and SLO detectors.

For the purpose of providing a fast fundus image, a Line Scanning Laser Ophthalmoscope (LSLO) is generally faster than the SLO and equally useful, as is the line-scan ophthalmoscope (LSO) of U.S. Patent Publication No. 2006/0228011.

In a preferred embodiment, high quality (resolution) tomograms are provided in conjunction with an OCT data cube that provides context for them. The OCT data cube is registered with the high resolution scans by virtue of being acquired with the same optics. The data cube can provide a fundus image, retinal thickness maps, or other reductions of the volume data, to provide context for the high quality tomograms.

An OCT data cube provides context for any tomogram extracted from the cube. One would like to have high definition tomograms, with transverse spacing of A-scans comparable to the width of the probe beam (the transverse optical resolution). However, time and data storage constraints make it difficult to collect sufficiently many A-scans within the cube for every tomogram to have such high definition.

Often the clinician will concentrate only on one or two tomograms within the volume. It is efficient then to spend time and storage space on a few high definition tomograms, covering the remainder of the volume with relatively coarsely-spaced A-scans.

In application to imaging the retina, a cube covering the area of retina corresponding to 20° visual field is covered with a square array of A-scans. Preferably between 100×100 and 500×500 A-scans cover the volume, though the number may be either greater or smaller. The A-scans in the cube may be spaced between 0.2° and 0.04°, while the $1/e^2$ diameter of the OCT beam at the retina corresponds to 0.05°, so there are gaps between the tissue sections sampled by adjacent A-scans. In addition to the cube, we acquire two B-scans consisting of higher density A-scans than used to scan the volume, covering 20°. The high density A-scans are preferably spaced between 2 and 20 times closer together than the lower density A-scans used to cover the cube. Spacing A-scans more closely continues to give benefits, even when the spacing between A-scans is about half the beam diameter. In a preferred embodiment, at least 500 and more preferably at least 1000 A-scans are used to generate each B-scan.

The results of one such composite scan are shown in FIG. 1. FIG. 1 includes an en face view in the upper left quadrant and two high resolution tomograms, one in the upper right and the other in the lower left quadrants. The en face view comes from integration of the OCT data along the beam direction, giving an image similar to that of a scanning ophthalmoscope. In FIG. 1, we see the en face view with two tomograms taken from the same volume. The displays in the upper left and lower right quadrants are high density/resolution B scans. The red horizontal and yellow vertical lines in the en face image show the clinician the location of the high resolution B scans. The icon in the upper left corner of the high resolution B scans contains a color coded component to associate it with the location identified in the en face view.

In FIG. 2, the high density/resolution B scans have been replaced by their reverse video images. The gray scale is inverted in the tomograms, with black representing more light scattered from tissue, to better show the detail. Depending on the design and performance of the OCT system, a third cut of the volume, with constant depth, may also be attainable in high definition.

FIG. 3 shows tissue thickness maps derived from a 3D block of OCT data, with the high definition tomograms plotted to the right. (The black and white image of the retina, over which the thickness map is overlaid, is from a scanning ophthalmoscope.)

Figure 4:
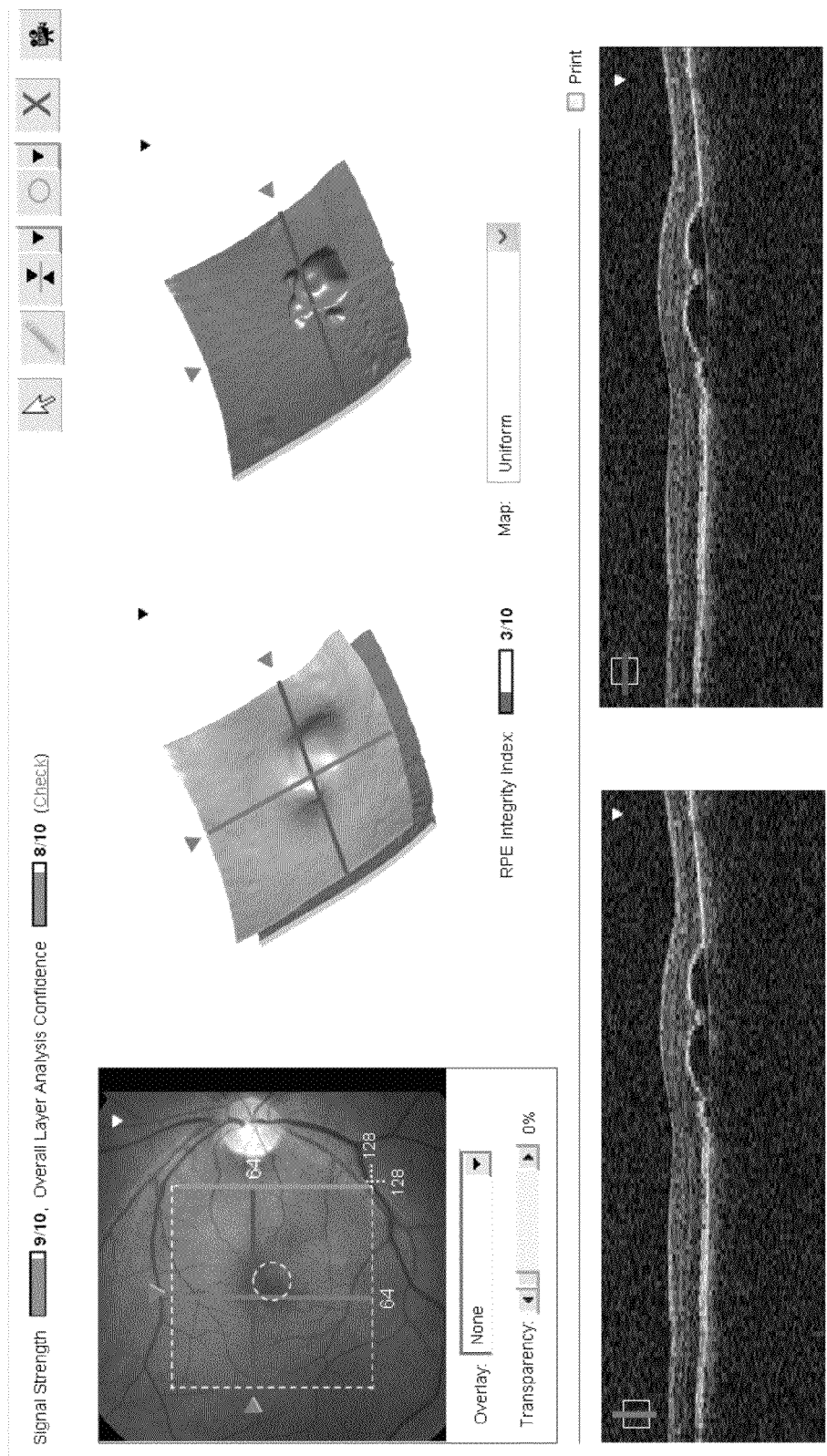
FIG. 4 is a display showing two high resolution scans in conjunction with displays of tissue surfaces extracted from the lower resolution scans.

FIG. 4 shows images of two high definition scans presented with surfaces extracted from the 3D block of OCT data. Indicia are provided on each of the views to help provide context. For example, the bottom left hand high definition image includes a small square in the upper left corner with a green bar. The location of the green bar within the square generally shows the location of the slice within the cube. Moreover, this indicator (green bar within a square) is overlaid on the lower density en face image. Here the green bar directly shows the clinician where within the larger cube the slice has been taken. The bottom right hand high definition image is similarly identified with a blue bar in both the high definition image and on the en face image.

While the description here describes a lower density cube and a small number of higher density planes, it is generally understood that one versed in the art can see the application of general volumes collected with lower density scans and a small number of higher density surfaces. For example, one or more high resolution circle scans are acquired, with companion lower density cube scan. A circle scan is particularly useful for evaluating the health of the retina by use of retinal layer thickness measurements. Multiple neighboring high resolution circle scans are useful for improving thickness measurements, for example by averaging thickness measurements or improving boundary detection. FIG. 5 is a display of an en face image on the left hand side coupled with a high resolution compound circle scan on the right hand side.

The high definition B-scans in the example of FIG. 1 were acquired before the cube, but they may also be acquired after the cube or in the middle of acquiring the data cube. The composite scans are acquired in conjunction with the motion-correction method described in U.S. Patent Publication 2006/0164653 cited above. Briefly, a sparse set of A-scans is taken before or after the composite scan, so that the high definition scan and the cube can both be corrected for patient motion. When one or more high definition B-scan is acquired first, especially when at least one such scan is taken along the slow-scan direction of the volume, it/they may be used to help in motion correction, even though this is not their primary purpose. When used in this manner, it is advantageous to collect the high density scans first. The composite scans can also be acquired in conjunction with tracking by the LSLO as described in U.S. Patent Publication No. 2006/0228011, cited above, so that transverse motion of the eye is corrected during data acquisition.

Alternatively, a high resolution cube scan can be acquired, constrained within a volume imaged by a lower density cube scan. A high resolution volume scan can even be acquired which contains the lower density volume scan. When the high resolution volume scan covers a small volume, for example of the macula or the optic nerve head, in some cases it can be acquired so quickly that the probability of motion over the acquisition time is low. However, acquisition of large high density volumes can require sufficient time for acquisition that motion occurs. In this case, the lower density volume can be used to correct for motion in the high resolution volume. The lower density volume may itself have been corrected for motion using a sparse set of A-scans.

The high definition scans provide a good starting point for image segmentation. Some factors that help in segmentation are the over-sampling of the speckle in the high definition image, and the higher sensitivity coming from reduced motion artifact. Several techniques exist for extending a segmented tomogram to neighboring tomograms, so segmentation of the entire cube can be improved by the presence of the high definition scans.

Presentation of the high definition scans in context of the cube can now be performed in a number of effective ways. Straightforward volume rendering, in which the high definition scans naturally stand out, shows the high definition scans in 3-dimensional context. Also effective is a plot of the high definition scans in perspective, over a base map consisting of an en face projection, macular thickness, or any other map from the 3D scan.

The data resulting from the volume acquisition in such a composite scan can be significantly reduced in size, but reduced in ways that keep important information to provide context for the high definition scans. The data cube can be reduced to an en face image, and/or a retinal thickness map, and/or an RNFL map, for example.

The presentation can be reduced in size as well, showing OCT-generated en face images, macular thickness or other maps, and high definition tomograms all on one sheet, screen, or report.

In its broad form, the concept includes operating the scanner of an OCT device to obtain a first set of high resolution measurements at a plurality of locations along a first line in the X-Y plane. The scanner of the OCT is also arranged to collect a data cube based on a second set of lower resolution measurements at a plurality of locations across the X-Y plane. The average spacing between the locations for the data cube is larger than the average spacing for the high resolution measurements. In a preferred embodiment, the average distance between adjacent locations for the high resolution measurements is less than twenty five percent (and more preferably less than ten percent) of the average distance between locations in the lower resolution measurements. These results can be stored in memory and displayed as shown in FIGS. 1 to 5.

In a preferred embodiment, wherein the high resolution measurement scans are taken first, it is desirable that the second set of lower resolution measurements be initiated less than four seconds after the high resolution measurements had been initiated. Ideally, the lower resolution scan automatically starts following the high resolution scan.

The high resolution measurements are preferably along a line. The line could be curved or straight. In a preferred embodiment, two high resolution line scans are performed, perpendicular to each other. The results of such a measurements are shown in the top two quadrants of FIG. 1.

Repeat Scans

The previous section described a thickness map derived from the 3D OCT data blocks overlaid on ophthalmoscope images (FIG. 3). The en face view from integrated intensity maps is valuable in later visits to repeat OCT data collection from the same tissue. The operator sees a live ophthalmoscope fundus image from the ophthalmoscope with an overlay of a scan pattern and a semi-transparent version of the en face image from the previous OCT data cube. FIG. 6a is an ophthalmoscope fundus image and FIG. 6b is an en face OCT intensity map. FIG. 6c shows the en face OCT image overlaid on the ophthalmoscope fundus image.

The operator manually registers these two images by adjusting a fixation target position and/or moving the scan location. FIG. 6d shows the overlay correctly adjusted. Optionally, if sufficient computational resources are available, the image can be overlaid and adjustments to the fixation target position may be made automatically.

In the illustrated embodiment, the overlay is an en face integrated image derived from OCT data and the underlying image is from the ophthalmoscope. Those skilled in the art will understand that other variations are possible. For example, the en face image can be displayed with an overlay of a portion of the ophthalmoscope image. Alternatively, alignment can be achieved by comparing a stored ophthalmoscope image overlaid with a current ophthalmoscope image. Similarly, alignment can be achieved by comparing a stored OCT image (en face or other image) overlaid with a current OCT image. In all cases, the alignment of the system is adjusted so that the currently obtained image matches a previously obtained image. The previously obtained image could have been derived from an earlier visit by the patient.

Alignment can be obtained by moving the patient's eye, and hence the live underlying image, or by moving the optical imaging alignment, and hence moving the overlaid image since it is aligned with the optical axis. In practice, when the fixation target has limited locations, only rough alignment is achieved through eye motion and the fine adjustment of the alignment is achieved by optical alignment of the galvos.

Various ways can be used to improve the usability of the overlay. The overlay can be semi-transparent or patterned. The overlay can have a checkerboard pattern or a striped pattern, where a portion (say half of the squares or stripes) of the pattern is totally transparent. Various colors can be used to enhance the user's ability to see alignment. One such color scheme converts the grayscale ophthalmoscope image to shades of red while changing the grayscale of the overlay. When bright regions align, the red and green add to make a new color, like yellow. Similarly, when dark regions align they create a darker region because, when they were misaligned, the misaligned color creeps into and brightens the region.

Standardization of Orientation

OCT images of the back of the eye are typically acquired by sending light in and out through the human pupil. The orientation of the data in the resulting OCT data cubes changes slightly with the position of the OCT beam in the pupil. In order to properly compare measurements between visits, the orientation of the data should be standardized. This standardization of orientation can be achieved by identifying an anatomical layer such as the retinal pigment epithelium and rotating the OCT data blocks, either to a standard orientation of that layer, or to match the orientation of that layer. Methods to find a reliable surface and present OCT data relative to that surface are described in co-pending U.S. patent application Ser. No. 11/223,549, cited above.

Another standardization of orientation can be achieved by orienting segmented surfaces in a standard orientation for display. It is advantageous that the view is standardized to enable visit-to-visit correspondence between the displays. The view of the ILM (inner limiting membrane) is preferably oriented to show peaks and valleys of the surface. This orientation should match the orientation of the combined RPE/mM map.

Figure 7:
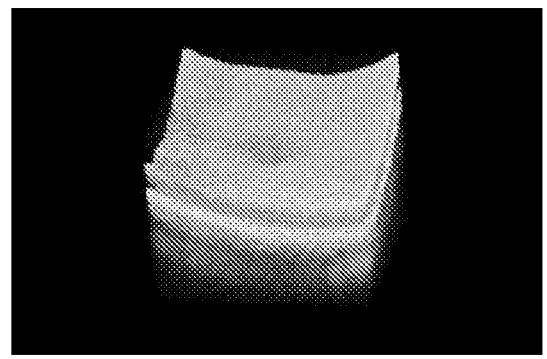
FIG. 7 is a 3D volumetric rendering of OCT image data.
Figure 8A:
FIGS. 8a and 8b are layer maps shown in different spatial orientations.
Figure 8B:

Examples of this concept are illustrated in FIGS. 7 and 8. The densely sampled volumetric data collected by the OCT scanner can be displayed as a 3D volumetric rendering (FIG. 7) or represented more abstractly as layer maps (FIGS. 8a and 8b). The orientation of the tissue (retina) can vary from one scan to the next in relation to optical axis and thus the cube of data (FIG. 8). As a result of this variability in orientation, the clinician does not always have the same view of the tissue from one patient visit to the next. As noted above, it would be very beneficial to the clinician if he/she were able to see the 3D representation of the tissue in the same orientation regardless of the variation in the imaging axis. To optimize/normalize the viewing angle, an algorithm can estimate the orientation of the tissue in respect to the data coordinate system (cube of data) and automatically rotate the 3D image such that the tissue would always appear in the same orientation (in respect to the "rendering" coordinate system). By doing so, the doctor will see the tissue in the same orientation and therefore will be more effective in comparing the tissue/pathology from one visit to the next. Without an automated algorithm the operator will have to spend tens of seconds to orient each scan and will likely result in inconsistencies from one operator to the next.

In is broad form, the subject method requires analyzing the OCT data to determine the orientation of the image. Thereafter, the image is rotated to a preferred orientation and this resulting image is displayed. The image can be rotated to best view a particular structure, to match a previous view derived from data obtained at an earlier time or to maximize viewing of features of interest.

Diagnostic Metrics of Texture and Heterogeneity

Various pathologies of the eye can cause non-uniformities which can be imaged and or analyzed. This aspect of the subject invention relates to identifying such non-uniformities and generating images of the non-uniformities. Alternatively, once the non-uniformities are identified, they are quantified in a manner to aid in the diagnosis of a disease state.

One example of a non-uniformity in the eye are drusen. Drusen are small mounds of amorphous material deposited within Bruch's membrane by cells in the retinal pigment epithelium (RPE) in cases of age-related macular degeneration. The presence of many drusen of diameter greater than 100 microns can be a predictor of retinal atrophy or choroidal neovascularization. In an OCT scan, drusen appear as mildly reflective regions causing shallow elevations in the RPE. By using a volume-scanning OCT system, these regions may be identified and indicated in an en face view of the scanned region. After the detection of drusen larger than 100 microns, a map can be generated indicating the locations of such large drusen in an en face fundus view. Either the extent or just the center of such drusen could be indicated in the map.

Without needing to detect individual drusen, a map of the roughness of the RPE could indicate the presence and general location of drusen. Roughness may be defined as the root-mean-squared vertical deviation of the RPE boundary about a local mean or a surface fitted to an RPE segmentation. Other equivalent metrics of deviation in elevation or complexity of the surface texture may also be used. Roughness could also be defined in terms of variation in brightness along the RPE or a smoothed or fitted version of the RPE. Such a map of roughness could also be constructed for the vitreo-retinal interface as an indicator of glaucoma.

For diabetic macular edema, the presence of hard exudates is indicative of the resorption of serous fluid from leaking capillaries. These lesions will appear in an OCT scan as small bright spots above the RPE that may be detected by thresholding and possibly by the presence of shadows. The presence of hard exudates in the fovea will impair central vision, so a map of these heterogeneities marked with the location of the fovea could be useful in explaining vision deficits.

Maps of other characteristic parameters of heterogeneity such as the density or average size of drusen or exudates could also prove to have clinical utility. For example, estimates of drusen volumes can be achieved by computing the volume bounded by the RPE and a smoothed surface RPE fit, constrained within the field of view. In fact, volume measurements can be achieved measuring the volume bounded by any two segmented surfaces or the volume bounded by any two surfaces determined from the volume data. Either surface may be acquired through segmentation, heuristically acquired, estimated by fitting any known surface to data, or any other means for stipulating a surface. Once the two surfaces are defined, measurements can be made either of the volume between the two surfaces or the surfaces can be subtracted and either positive or negative volumes can be computed from the difference surface and any fixed plane, bounded within the field of view. Other measures can be made on one of the surfaces by itself, such as the total area of the surface, area of the surface exceeding a specified height, or any measure of the variation of the surface. Still other measures can be made as functions of the two surfaces, such as the variation of the surface defined be the difference between the two surfaces or the area of the domain of all points of the difference surface that exceed a given height. Displays can be presented of these volumes, surfaces, or areas or values can be tabulated for volume or area or other values functionally dependent on these data.

Macular edema can manifest itself as a diffuse swelling or as the formation of cysts in the retina. The OCT image (or the undemodulated image data, which represents a linear combination of scatterer responses) may be analyzed to give tissue texture parameters that can indicate the degree of cyst formation. These parameters may include width or side lobe height of the autocorrelation function, statistics of intensity, or a combination of these. Such a map of sponginess or porosity would help identify the presence of diffuse (or both cystic and diffuse) fluid in tissue. The distribution of cyst sizes could be indicated with a metric such as such as average fluid-space diameter to characterize the diffuseness of the edema. Other measures, such as the volume between two surfaces, statistics such as the mean distance between two surfaces or the standard deviation of the mean distance between two surfaces are measures of the size of the swelling. 3-D displays of differences of two surfaces, 2-D displays of the height (encoded in color or grayscale) of a surface or maps of the distance from a point on a surface to another surface, or 2-D binary displays of the points meeting some criteria can be used to visualize measures of the edema. Equivalently, measures of volumes or areas satisfying some criteria may be tabulated and displayed.

Metrics of texture could also be used to quantify the clarity of cystic spaces and/or vitreous humor. Clear dark fluid in these spaces indicates the absence of cells, which are an indicator of inflammation and/or infection. If cells were present in these areas, one would expect increased reflectivity characteristic of isolated scatterers, eventually developing into full speckle. The difference between background noise, isolated scatterers, and full speckle could be indicated by such statistical indicators as the ratio of the mean intensity to the standard deviation of intensity, or the axial and lateral autocorrelation function widths and side lobe heights.

Although the above concepts have been described as two-dimensional en face maps of texture and heterogeneity metrics, the same notions could be applied to three-dimensional representations or three-dimensional renderings of surfaces containing these metrics as functions of the two lateral dimensions. Also, scalar summary metrics of these features, such as average values and/or deviations of these metrics over the imaged volume, may serve a similar purpose.

Drusen or hard exudates may be identified using a fundus camera, but the use of OCT data has the potential for more reliable detection, given the additional information in the depth axis. Due to the absence of depth information from fundus photography, a roughness analysis of the RPE or VRI, a porosity analysis for macular edema, or a textural identification of cyst inflammation would simply not be possible.

In a preferred approach, the non-uniformities can be displayed with reference to a landmark within the eye. Here, the term landmark is intended to include features such as the fovea, vessels, lesions, the fundus image itself, fluid regions, anatomical features and pathological features. A collection of landmarks can itself be a landmark. Included in the definition of textures: roughness, clarity, reflectivity, connectedness and elevation.

Retinal Fluid Maps

Another type of non-uniformity of interest is associated with cystic regions of retinal fluid.

Although diffuse edema is a common characteristic of retinal disease, cystic regions of fluid can be located and delineated using analysis of 3-D OCT scans. Intraretinal fluid usually occurs as cystic edema in the outer nuclear and outer plexiform layers. Subretinal fluid will pool into clearly defined areas just above the RPE, while choroidal disease is characterized by prominent pockets of fluid below the RPE.

Three-dimensional raster scanning of the retina facilitates the creation of detailed 2-D maps of the retina analyzed by depth. Maps of intraretinal, subretinal, and/or sub-RPE fluid can help diagnose the existence and progress of exudative retinal disease.

Fluid can be detected by thresholding of the retinal images, followed by a removal of small regions below that threshold (to remove voids due to speckle or shadows). Voids in the retina that do not approach the RPE (as detected by a separate segmentation process) would be classified as intraretinal, while pockets that border the RPE would be characterized as subretinal. Sub-RPE fluid could be approximately defined by fitting a smooth surface such as a paraboloid to the RPE (see U.S. application Ser. No. 11/223,549, cited above) and its discussion of referencing the elevation of the RPE to that surface fit. Pronounced pockets of fluid would stand out from the fitted surface and appear as spots on an otherwise blank map. FIG. 9 is an en face map of RPE elevation in microns relative to a surface fitted to the RPE. Detachments of the RPE stand out in light regions.

FIG. 10 is an en face map showing root-mean-squared deviation of the RPE depth about the local mean depth. The red and yellow patches in the superior half of the field represent small inhomogeneities, likely drusen, while the white-and-yellow ring below indicates a large, smooth inhomogeneity, likely an RPE detachment. FIG. 11 is a B-scan showing the detection of small voids larger than the normal dark spots that are due to speckle. FIG. 12 is an en face map showing the density of voids in the retina. Yellow indicates an elevated density while red indicates the highest densities.

As with the textural maps, the fluid-pocket information could be presented in a wide variety of formats. Two-dimensional en face maps or images of texture and heterogeneity metrics could optionally be applied to three-dimensional representations or three-dimensional renderings of surfaces containing these metrics as functions of the two lateral dimensions. Also, scalar summary metrics of these features, such as average values and/or deviations of these metrics over the imaged volume, may serve a similar purpose.

FIG. 13 is a B-scan showing the presence of fluid both below and above the RPE, but below the neurosensory retina. FIG. 14 is an en face map showing the depth of fluid in microns between the RPE and a parabolic surface fitted to the RPE. FIG. 15 is an en face map showing the depth of fluid in microns in the vicinity just above the RPE. Compared to the map of FIG. 14, one can see the subretinal fluid is clustered at the "shoulders" of the large RPE detachments indicated in the map of sub-RPE fluid.

Integrated Intensity

A primary concern of the OCT analysis of the retina is the integrity of the tissue following degenerative diseases. A map of the integral of reflectivity above the RPE (perhaps normalized to RPE reflectivity or overall intensity in the A-scan) may have value as an indicator of prognosis after healing. Integrated intensity within the RPE itself may be indicative of AMD, atrophic RPE, and Retinitis Pigmentosa. Below this, the integrated intensity in the choroid, taken as a percentage of overall integrated reflectivity, may similarly indicate RPE atrophy, RPE bleaching, retinal atrophy, etc. Images or maps of these parameters could be viewed in a 2-D or 3-D format and possibly combined with representations of other retinal parameters.

Just as intensity can be integrated above the RPE, it can be integrated either above or below any surface, either detected in or determined from the data, or established a priori. Intensity can also be integrated between two surfaces, such as from the ILM to the RPE, or from the RPE to some fixed N pixels (or voxels) above (or below) the RPE.

Further information about integrated intensity maps can be found in U.S. Patent Publication No. 2006/0119858, incorporated herein by reference.

3D Analysis of Membrane Geometry to Identify Traction Forces

Posterior Hyaloid and epiretinal membranes can pull on the retina, causing its deterioration. Surgical removal of these membranes must be done carefully so as not to further damage the retina during the removal. Knowing the degree and direction of the tractional forces on the retina would be useful for diagnosing whether membrane removal is indicated. If surgery is performed, such knowledge would help determine the best points to detach and in what directions to apply traction when removing the membrane. Traction force could be estimated by looking at the tautness of the membrane and other nearby points of attachment. This information could be displayed as overlays for en face images that show attachment points color-coded with estimated traction force (or a clinically relevant component of force, such as the component that is normal to VRI, normal to RPE, or the total magnitude) or a metric of local surface curvature. One could also similarly color membranes in cross-sectional B-scans using this information.

Another visualization would be to extract a cross-section perpendicular to the contour of the membrane attachment and identify the presence of holes underneath points of attachment. From an en face view indicating the points of attachment, a user could scroll along the contour where the membrane attaches and view the stage of hole formation based on a thorough exam of all attachment points. The stage assessment could possibly be automated as well, giving an en face view of the data indicating the points of attachment with, e.g., green contours showing points of attachment with no hole formation, yellow showing attachments with a mild hole formation, and red showing attachments with underlying holes of an extreme stage.

FIG. 16 is an en face view indicating points of membrane attachment. FIG. 17 is an en face map showing points where membranes approach the vitreo-retinal interface (VRI) and the curvature of the VRI at that point. The dark green areas have no membrane detected near the retina, while the light green area shows membranes in proximity to the retina but little or no evidence of pulling on the VRI. Yellow areas have some membrane traction indicated by the VRI curvature, while the red areas have the sharpest peaking in the VRI, indicating strong traction. FIG. 18 is a horizontal B-scan through a point of high membrane traction as indicated in red on the traction map. The orientation of the B-scan could be automatically selected according to the membrane and retina geometry. FIG. 19 is a Diagonal B-scan composed of lines extracted from a set of parallel horizontal B-scans. The direction of this B-scan is perpendicular to the ridge in the VRI, thus showing a higher angle of membrane attachment (even when larger line spacing is taken into account).

In its broad form, this concept includes the steps of identifying membrane attachments to the retina from OCT image information and displaying a map illustrating the identified membranes. The display could illustrate tautness of the membranes or the disruption of layers. We can display suspect B-scans, allowing the operator to determine if there are actual holes. The maps can be displayed with respect to a larger field of view (the SLO). We can also reference the epiretinal membrane (ERM). The distortion of the ERM can be correlated with retinal layer disruption.

Binary Maps

When attempting to differentiate healthy from diseased tissue, measures are often thresholded. Various thresholds are often set depending on confidence and/or reliability. FIG. 20 is a flowchart for how to convert a surface, segmented from a 3-D volume and into a binary image. Areas of concern can be measured by simple pixel counts converted to area. Examples of such binary maps are provided in FIGS. 21 and 22

The left hand displays of FIG. 21 shows RPE elevation maps. The two displays on the lower right are two binary maps with different threshold levels. The area covered by the white pixels (where data exceeded the threshold) is a measure of the likelihood of disease. FIG. 22 is similar to FIG. 21 but illustrates the situation where there are very few regions of concern. The membrane attachment map shown of FIG. 8 can be binarized where the threshold is chosen to measure membrane attachment.

In broad form, the method can include the steps of comparing OCT image data to a threshold and displaying a binary map of the data wherein points that exceed the threshold are displayed in one format and points that are below the threshold are displayed in a second format. In a preferred embodiment as indicated by the flowchart of FIG. 20, an elevational map can be generated and distances from the map to another tissue layer or boundary can be computed and compared to a threshold. This information can then be displayed in a binary map. The binary map can be displayed as an overlay on another image of the eye.

Figure 23:
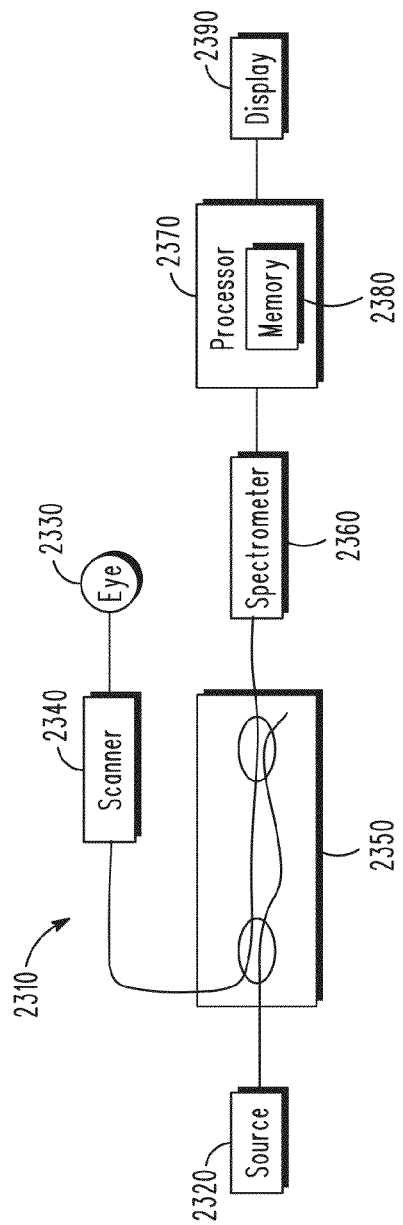
FIG. 23 is a diagram of an OCT system which can be used to implement the subject invention.

A simplified illustration showing the basic elements of an OCT system 2310 are shown in FIG. 23. Further details about OCT systems can be found in the various articles and patent citations set forth above as well as in U.S. Provisional Application No. 60/815,107, previously incorporated by reference.

OCT system 2310 includes a light source 2320 which can be a laser diode. A portion of the light is directed along a sample path to the eye 2330. The sample path includes a means 2340 for scanning the beam over the eye which can be a pair of galvanometer driven mirrors. Light returned from the eye is combined with light from the source in an interferometer arrangement 2350. The output of the interferometer is supplied to a detector which can be a spectrometer 2360. The output from the spectrometer is supplied to a processor 2370 which will include a memory 2380 for storing the results. The results can also be shown on a display 2390.

While the subject invention has been described with reference to the preferred embodiments, various changes and modifications could be made therein, by one skilled in the art, without varying from the scope and spirit of the subject invention as defined by the appended claims

I claim:

1. A method of displaying information related to an abnormal membrane attached to the vitreoretinal interface (VRI) of an eye based on 3D image data acquired by an optical coherence tomography (OCT) system comprising the steps of:
    identifying the location and extent of the attachments of the membrane to the VRI based on an analysis of the 3D image data; and
    displaying an image illustrating the location and extent of the attachments of the membrane to the VRI, said image providing a coded visual indication of the degree of tractional forces on the VRI based on the proximity of the membrane to the VRI and the curvature of the VRI.

2. A method as recited in claim 1, wherein said image indicates the tautness of membrane.

3. A method as recited in claim 2, wherein the level of tautness is indicated by color coding.

4. A method as recited in claim 1, wherein the image further indicates the disruption of tissue layers within the eye.

5. A method as recited in claim 1, wherein the membrane is displayed as an overlay with respect to an en face image of the eye.

6. A method as recited in claim 1, wherein said image further indicates holes associated with the membrane attachments.

7. A method as recited in claim 1, wherein said image includes B-scans of one or more orientations through a selected point of membrane attachment.

8. A method as recited in claim 7, wherein the orientation of the B-scan is automatically selected according to the membrane and VRI geometry.

9. A method as recited in claim 1 wherein the membrane is an epiretinal membrane.

10. A method as recited in claim 1 wherein the image indicates the magnitude of the force placed on the VRI by the membrane.

11. A method as recited in claim 1 wherein the image indicates a component of the force placed on the VRI by the membrane.

12. A method as recited in claim 11 wherein the component of the force indicated in the image is in a direction normal to the vitreo-retinal interface.

13. An optical coherence tomography (OCT) system for generating and displaying information related to an abnormal membrane attached to the vitreoretinal interface (VRI) of an eye comprising:
    a light source for generating a beam of light;
    a scanner for directing the beam to different locations within the eye;
    a detector for collecting 3D image information about the reflectance distribution within the eye;
    a processor for identifying the location and extent of the attachments of the membrane to the VRI based on an analysis of the 3D image information; and
    a display for displaying an image illustrating the location and extent of the attachments of the membrane to the VRI, said image providing a coded visual indication of the degree of tractional forces on the VRI based on the proximity of the membrane to the VRI and the curvature of the VRI.

14. A system as recited in claim 13, wherein said image indicates the tautness of membrane.

15. A system as recited in claim 14, wherein the level of tautness is indicated by color coding.

16. A system as recited in claim 13, wherein the image further indicates the disruption of tissue layers within the eye.

17. A system as recited in claim 13, wherein the membrane is displayed as an overlay with respect to an en face image of the eye.

18. A system as recited in claim 13, wherein said image further indicates holes associated with the membrane attachments.

19. A system as recited in claim 13, wherein said image includes B-scans of one or more orientations through a selected point of membrane attachment.

20. A system as recited in claim 19, wherein the orientation of the B-scan is automatically selected according to the membrane and VRI geometry.

21. A system as recited in claim 13 wherein the image indicates the magnitude of the force placed on the VRI by the membrane.

22. A system as recited in claim 13 wherein the image indicates a component of the force placed on the VRI by the membrane.

23. A system as recited in claim 22 wherein the component of the force indicated in the image is in a direction normal to the vitreo-retinal interface.

24. A method as recited in claim 1 wherein the extent of the attachment is indicated by color coding.

25. A system as recited in claim 13 wherein the extent of the attachment is indicated by color coding.

* * * * *

UNITED STATES PATENT AND TRADEMARK OFFICE
CERTIFICATE OF CORRECTION

PATENT NO. : 8,764,189 B2  
APPLICATION NO. : 13/240701  
DATED : July 1, 2014  
INVENTOR(S) : Paul F. Stetson It is certified that error appears in the above-identified patent and that said Letters Patent is hereby corrected as shown below:

On Title page 2, in column 2, References Cited under "Other Publications", line 43, delete "Distrubution" and insert -- Distribution --, therefor.

On Title page 3, in column 1, References Cited under "Other Publications", line 13, delete "CoherenceTomography" and insert -- Coherence Tomography --, therefor.

On Title page 3, in column 1, References Cited under "Other Publications", line 55, delete ""Comeal" and insert -- "Corneal --, therefor.

On Title page 3, in column 2, References Cited under "Other Publications", line 47, delete "Coherencetomography"," and insert -- Coherence tomography", --, therefor.

In the Specification

In column 8, line 36-37, delete "RPE/Mm" and insert -- RPE/ILM --, therefor.

In column 9, line 3, delete "and or" and insert -- and/or --, therefor.

In column 13, line 8, delete "22" and insert -- 22. --, therefor.

In column 13, line 49, delete "claims" and insert -- claims. --, therefor.

Signed and Sealed this  
Twenty-third Day of September, 2014

Michelle K. Lee  
*Deputy Director of the United States Patent and Trademark Office*